United States Patent
Schubert et al.

(10) Patent No.: US 10,190,978 B2
(45) Date of Patent: Jan. 29, 2019

(54) OPTICAL SENSING AND SEPARATION BASED ON ORDERED 3D NANOSTRUCTURED SURFACES

(71) Applicant: NUtech Ventures, Lincoln, NE (US)

(72) Inventors: Mathias M. Schubert, Lincoln, NE (US); Tino Hofmann, Lincoln, NE (US); Daniel Schmidt, Petaluma, CA (US); Patrick H. Dussault, Lincoln, NE (US); Andrea Holmes, Crete, NE (US); Rebecca Y. Lai, Lincoln, NE (US)

(73) Assignee: NUtech Ventures, Lincoln, NE (US)

( * ) Notice: Subject to any disclaimer, the term of this patent is extended or adjusted under 35 U.S.C. 154(b) by 0 days.

(21) Appl. No.: 15/682,176

(22) Filed: Aug. 21, 2017

(65) Prior Publication Data

US 2018/0024055 A1    Jan. 25, 2018

Related U.S. Application Data

(62) Division of application No. 14/054,504, filed on Oct. 15, 2013, now Pat. No. 9,739,710.

(60) Provisional application No. 61/713,819, filed on Oct. 15, 2012.

(51) Int. Cl.
| | |
|---|---|
| *G01N 21/47* | (2006.01) |
| *G01N 21/23* | (2006.01) |
| *G01N 21/21* | (2006.01) |
| *G01N 21/3581* | (2014.01) |
| *G01N 21/25* | (2006.01) |

(52) U.S. Cl.
CPC ............ *G01N 21/47* (2013.01); *G01N 21/23* (2013.01); *G01N 21/211* (2013.01); *G01N 21/253* (2013.01); *G01N 21/3581* (2013.01)

(58) Field of Classification Search
CPC ....... G01N 21/47; G01N 21/23; G01N 21/211
USPC .......................................................... 356/365
See application file for complete search history.

(56) References Cited

U.S. PATENT DOCUMENTS

| | | | | |
|---|---|---|---|---|
| 6,485,703 | B1 * | 11/2002 | Cote ................. | A61K 49/0041 424/9.1 |
| 6,697,144 | B2 * | 2/2004 | Kralik ................ | G02F 1/1334 349/115 |
| 7,011,878 | B2 * | 3/2006 | Nishizawa ......... | G11B 7/24056 156/272.2 |
| 8,323,772 | B2 * | 12/2012 | Lin ..................... | B82Y 20/00 359/599 |
| 9,298,041 | B2 * | 3/2016 | Escuti ................ | G02B 5/3083 |
| 9,739,710 | B2 * | 8/2017 | Schubert ............ | G01N 21/23 |

(Continued)

OTHER PUBLICATIONS

Angeloni et al, "Suppression of the metal-insulator transition temperature in thin $La_{0.7}Sr_{0.3}MnO_3$ films," *J. Appl. Phys.*, 2004, 96: 6387-6392.

(Continued)

*Primary Examiner* — Roy M Punnoose
(74) *Attorney, Agent, or Firm* — Fish & Richardson P.C.

(57) ABSTRACT

A sensor having a substrate is provided in which structures are disposed on a surface of the substrate. The structures can be, e.g., nanostructures. Polarized light is directed toward the sensor, and birefringence of the structures with respect to the light is measured. Target particles that interact with the structures are detected based on changes in the measured birefringence.

24 Claims, 19 Drawing Sheets

(56) References Cited

U.S. PATENT DOCUMENTS

| | | | | |
|---|---|---|---|---|
| 2002/0154261 | A1* | 10/2002 | Kralik | G02F 1/1334 349/117 |
| 2010/0028543 | A1* | 2/2010 | Davis | B22F 1/0025 427/372.2 |
| 2010/0164489 | A1* | 7/2010 | Lukaszew | G01N 33/54326 324/244.1 |
| 2014/0106980 | A1 | 4/2014 | Schubert et al. | |

OTHER PUBLICATIONS

Armstrong and Virkar, "Performance of Solid Oxide Fuel Cells with LSGM-LSM Composite Cathodes," *J. Electrochem. Soc.*, 2002, 149: A1565-A1571.

Arnold et al., "Broad Spectral Response Using Carbon Nanotube/Organic Semiconductor/$C_{60}$ Photodetector," *Nano Lett*, 2009, 9: 3354-3358.

Belyea et al, "Magnetocaloric effect in epitaxial La0.56Sr0.44MnO3 alloy and digital heterostructures," *J. Appl. Phys.*, 2012, 111: 07A935.

Bohigas et al, "Room-Temperature Magnetic Refrigerator Using Permanent Magnets," *IEEE Trans. Magn.* 36: 538-544 (2000).

Borisov et al, " Magnetoelectric Switching of Exchange Bias," *Phys. Rev. Lett.*, 2005, 94: 117203.

Chen and Yan, "Main Characteristics of a Brayton Refrigeration Cycle of Paramagnetic Salt," *J. Appl. Phys.* 75:1249 (1994).

Eerenstein et al, "Multiferroic and magnetoelectric materials," *Nature*, 2006, 442: 759-765.

Gong et al., "High-Detectivity Polymer Photodetectors with Spectral Response from 300 nm to 1450 nm," *Science*, Sep. 2009, 325:1665-1667.

Gschneidener et al, "Recent developments in magnetocaloric materials," *Rep. Prog. Phys.*, 2005, 68: 1479-1539.

He et al, "Robust isothermal electric control of exchange bias at room temperature," *Nature Mater.*, 2010 9: 579-585.

Huynh et al, "Hybrid Nanorod-Polymer Solar Cells," *Science*, 2002, 295: 2425-2427.

Jadhav et al, "Singlet Exciton Fission in Nanostructured Organic Solar Cells," *Nano Letters*, 2011, 11:1495-1498.

Jin et al, "Solution-Processed Ultraviolet Photodetectors Based on Colloidal ZnO Nanoparticles," *Nano Letters* (2008) 8: 1649-1653.

Kind et al, "Nanowire Ultraviolet Photodetectors and Optical Switches," *Advanced Materials*, 2002, 14:158-160.

Kline et al, "Highly oriented crystals at the buried interface in polythiophene thin-film transistors," *Nature Materials*, 2006, 5:222-228.

Knoll, *Radiation Detection and Measurement*, 3rd ed., 2000, John Wiley and Sons, Inc., 274-320.

Konstantatos and Sargent, "Nanostructured materials for photon detection," *Nature Nanotechnology*, 2010, 5:391-400.

Konstantatos et al, "Sensitive solution-processed visible-wavelength photodetectors," *Nature Photonics*, 2007, 1: 531-534.

Konstantatos et al., "Ultrasensitive solution-cast quantum dot photodetectors," *Nature*, 2006, 442:180-183.

Li and Chou, "Solar-blind deep-UV band-pass filter (250-350nm) consisting of a metal nano-grid fabricated by nanoimprint lithography," *Optics Express*, 2010, 18:931.

Liang et al., "ZnO Schottky ultraviolet photodetectors," *Journal of Crystal Growth*, 2001, 225:110-113.

Liu, "14.5 Junction photodiodes," *Photonic Devices*, 2005, 966-986.

Lu et al, "Electric modulation of magnetization at the BaTiO3/La0.67Sr0.33MnO3 interfaces," *Appl. Phys. Lett.*, 2012, 100: 232904.

Ma et al, "Recent Progress in Multiferroic Magnetoelectric Composites: from Bulk to Thin Films," *Adv. Mater.*, 2011, 23: 1062-1087.

McCulloch et al., "Liquid-crystalline Semiconducting Polymers with High Charge-Carrier Mobility," *Nature Materials* 5: 328 (2006).

Michalski et al, "Magnetic entropy changes in nanogranular Fe:Ni61Cu39," *J. Appl. Phys.*, 2011, 109:07A936.

Mukherjee et al, " Spin and elastic contributions to isothermal entropy change," *J. Appl. Phys.*, 2012, 111:07A931.

Mukherjee et al, "Magnetocaloric properties of Co/Cr superlattices," *Phys. Rev.*, 2009, B79: 144406.

Nozik et al., "Semiconductor Quantum Dots and Quantum Dot Arrays and Applications of Multiple Exciton Generation to Third-Generation Photovoltaic Solar Cells," *Chemical Reviews*, 2010, 110:6873-6890.

Pecharsky and Gschneidner, "Advanced magnetocaloric materials: What does the future hold?" *Int. J. Refrig.*, 2006, 29:1239-1249.

Pecharsky and Gschneidner, "Magnetocaloric effect and magnetic refrigeration," *J. Magn. Magn. Mater.*, 1999, 200:44.

Pecharsky and Gschneidner, "Giant Magnetocaloric Effect in Gd5(Si2Ge2)," *Phys. Rev. Lett.*, 1997, 78: 4494-4497.

Pecharsky et al, "The giant magnetocaloric effect of optimally prepared Gd 5 Si 2 Ge 2," *J. Appl. Phys.*, 2003, 93: 4722-4728.

Polisetty et al, "Piezoelectric tuning of exchange bias in a BaTiO3/Co/CoO heterostructure," *Phys. Rev.*, 2010, B82: 134419.

Provenzano et al, "Reduction of hysteresis losses in the Magnetic Refrigerant $Gd_5Ge_2Si_2$ by the addition of iron," *Nature* 429: 853 (2004).

Pyatakov and Zvezdin, *Phys. Usp.* 55: 557 (2012) (Eng Abstract).

Richard et al, "Magnetic refrigeration: Single and multimaterial active magnetic regenerator experiments," *J. Appl. Phys.*, 2004, 95:2146-2150.

Russek and Zimm, "Potential for cost effective magnetocaloric air conditioning systems," *Int. J. Refrig.*, 2006, 29:1366-1373.

Sahoo et al, "Ferroelectric control of magnetism in BaTiO3 / Fe heterostructures via interface strain coupling," *Phys. Rev.*, 2007, B76: 092108.

Salamon and Chun, "Griffiths singularities and magnetoresistive manganites," *Phys. Rev.*, 2003, B68: 014411.

Scott, "Electrocaloric Materials," *Annu. Rev. Mater. Res.*, 2011, 41: 229-240.

Skomski et al, "Entropy localization in magnetic compounds and thin-film nanostructures," *J. Appl. Phys.*, 2010, 107: 09A922.

Soci et al., "ZnO Nanowire UV Photodetectors with High Internal Gain," *NANO Letter*, 2007, 7: 1003-1009.

Sukhovatkin et al, "Colloidal Quantum-Dot Photodetectors Exploiting Multiexciton Generation," *Science*, 2009, 324: 1542-1544.

Sun et al, "Photovoltaic Devices Using Blends of Branched CdSe Nanoparticles and Conjugated Polymers," *NANO Letters*, 2003, 3:961-963.

Takahashi and Watanabe, "Recent Progress in CdTe and CdZnTe Detectors," *IEEE Transactions on Nuclear Science*, 2001, 48: 950.

Thiele et al, "Voltage-controlled epitaxial strain in $La_{0.7}Sr_{0.3}MnO_3$/$Pb(Mg_{1/3}Nb_{frax;2;3})O_3$—$PbTiO_3$ (001) films," *Appl. Phys. Lett.*, 2005 87: 262502.

Thiele et al, "Influence of strain on magnetization and magnetoelectric effect in La0.7A0.3MnO3 / PMN-PT(001) (A = Sr; Ca)," *Phys. Rev.*, 2007, B 75: 054408.

Wada and Tanabe, "Giant magnetocaloric effect of $MnAs_{1-x}Sb_x$," *Appl. Phys. Lett.*, 2001, 79: 3302-3304.

Wang et al, "Electric control of magnetism at room temperature," *Sci. Rep.*, 2012, 2: 223.

Wood and Potter, "General analysis of magnetic refrigeration and its optimization using a new concept: maximization of refrigerant capacity," *Cryogenics*, 1985, 25: 667.

Yang et al, "Electron spin resonance study of polycrystalline $La_{0.75}(Ca_xSr_{1-x})_{0.25}MnO_3$ (x = 0, 0.45, 1)," *J. Phys.: Condens. Matter*, 2009, 21: 046002.

Yoshikawa and Adachi, "Optical Constants of ZnO," *Jpn. J. Appl. Phys.*, 1997, 36: 6237-6243.

Ziese et al, "Coupled magnetic and structural transitions in $La_{0.7}Sr_{0.3}MnO_3$ films on $SrTiO_3$," *New J. Phys.*, 2008, 10: 063024.

Zimm et al, "Design and Performance of a permanent-magnet rotary refrigerator," *Int. J. Refrig.*, 2006, 29: 1302-1306.

\* cited by examiner

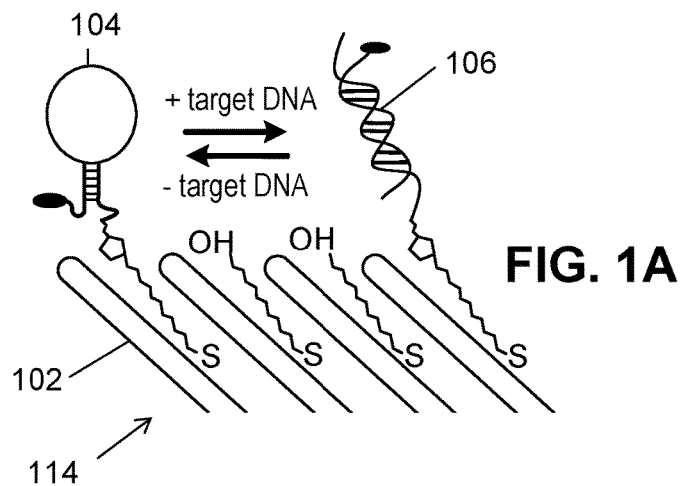
FIG. 1A
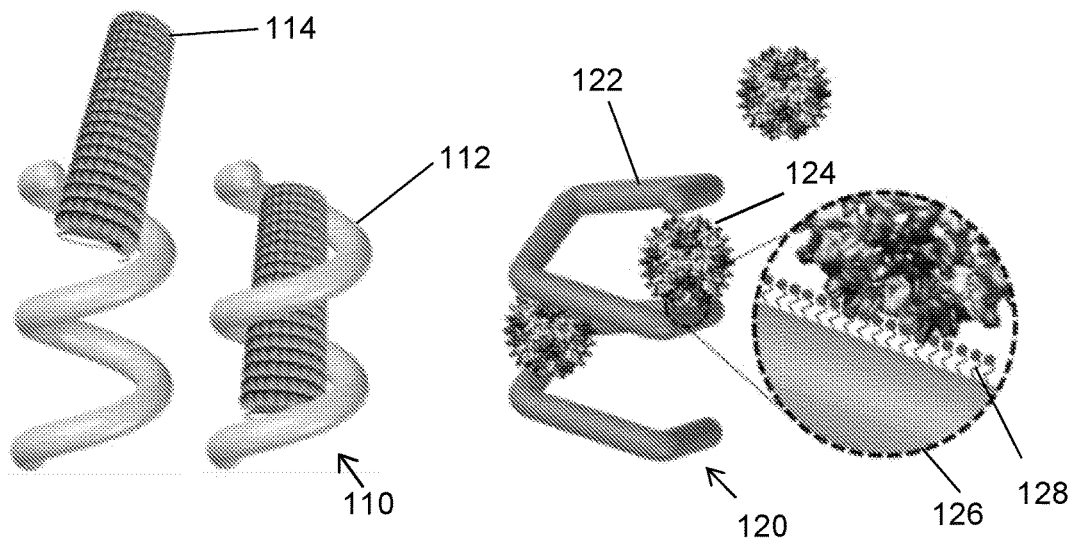
FIG. 1B
FIG. 1C

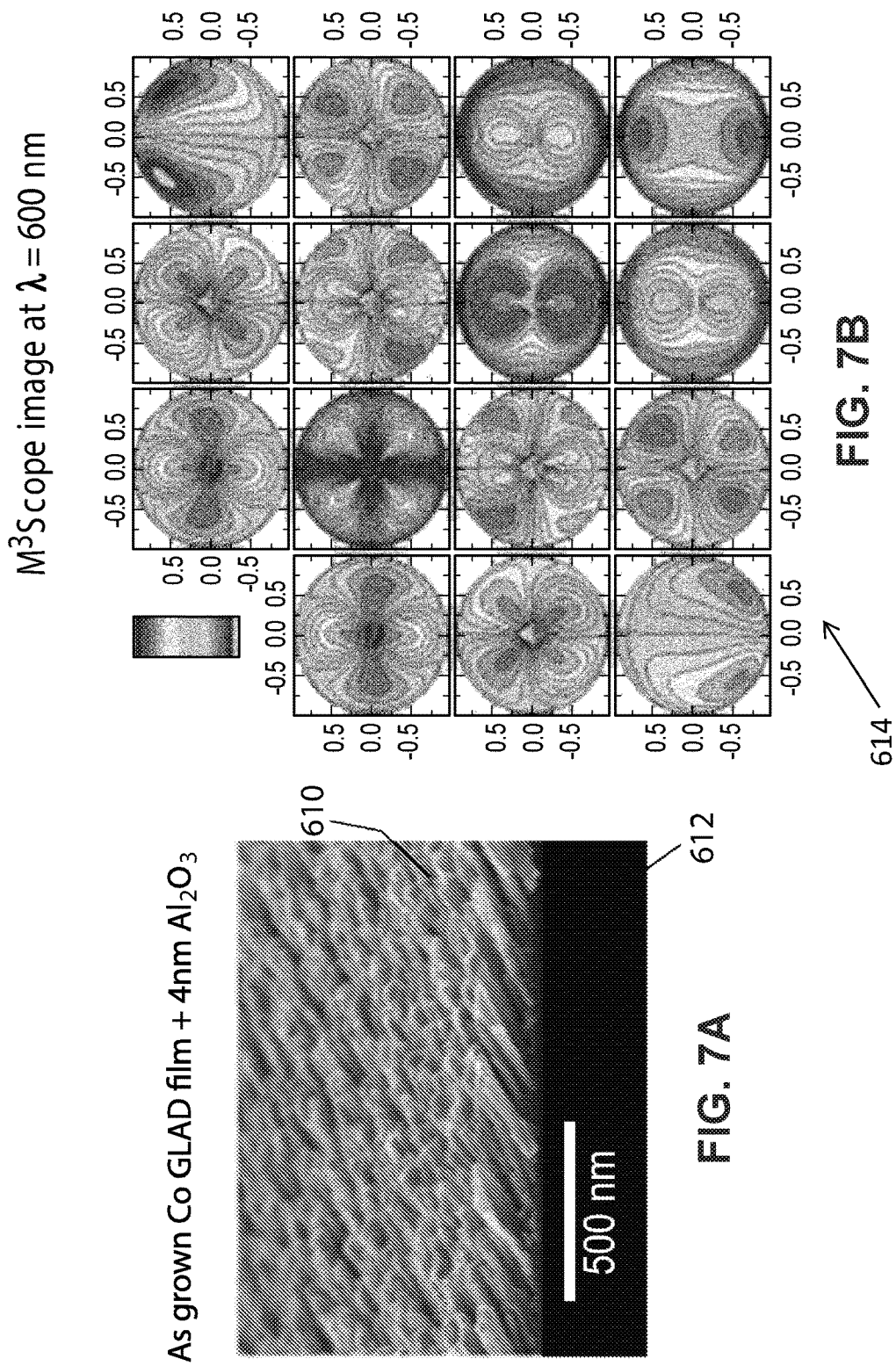

OPTICAL SENSING AND SEPARATION BASED ON ORDERED 3D NANOSTRUCTURED SURFACES

CROSS-REFERENCE TO RELATED APPLICATIONS

This application is a divisional application which claims priority to U.S. application Ser. No. 14/054,504 filed on Oct. 15, 2013, which claims priority to U.S. provisional application 61/713,819, filed on Oct. 15, 2012, which is incorporated herein by reference in its entirety.

STATEMENT AS TO FEDERALLY SPONSORED RESEARCH

This invention was made with government support under EPS1004094 awarded by the National Science Foundation. The government has certain rights in the invention.

TECHNICAL FIELD

This subject matter is generally related to optical sensing and separation based on ordered three-dimensional nanostructured surfaces.

BACKGROUND

A DNA microarray can be used to detect several types of nucleic acid sequences. In some implementations, the DNA microarray includes a substrate having strands of probe nucleic acid sequences. When a solution having unknown target nucleic acid sequences is applied to the microarray, the probe nucleic acid sequences on the substrate can bind to target complementary nucleic acid sequences in the solution. The target sequences can be labeled with fluorophores, and the probe-target pairs can be detected by detecting fluorescence emissions. The identity of the target sequences can be determined based on the positions of the detected fluorescence emissions on the microarray.

SUMMARY

In general, in one aspect, a method for detecting particles include directing light toward a sensor that comprises a substrate having structures disposed on a surface of the substrate; measuring birefringence of the structures with respect to the light; and detecting particles that interact with the structures based on changes in the birefringence.

Implementations of the method may include one or more of the following features. The structures can include nanostructures. The structures can have dimensions ranging from 1 nanometer to 100 micrometers. The structures can include columns, spirals, staircase structures, or chevron structures. The light can be polarized light. Measuring birefringence of the structures can include measuring polarization states of the structures. Measuring birefringence of the structures can include measuring birefringence using at least one of ellipsometry or polarimetry. Measuring birefringence of the structures can include measuring birefringence based on Mueller matrix microscopy. A first portion of the substrate can have structures that interact with the particles, and a second portion of the substrate can have structures that do not interact with the particles, and detecting the particles can include comparing a birefringence measurement of the structures on the first portion of the substrate and a birefringence measurement of the structures on the second portion of the substrate.

The method can include detecting light reflected from the substrate, in which measuring birefringence can include measuring birefringence based on the light reflected from the substrate. The method can include detecting light transmitted through the substrate, in which measuring birefringence can include measuring birefringence based on the light that is transmitted through the substrate. Detecting particles can include detecting peptides, DNA segments, RNA segments, capsids, antibodies, or viruses. Detecting particles that interact with the structures can include detecting particles that are captured by the structures.

The substrate can have portions having different types of structures that each interact with a corresponding type of particles. The method can include determining at which portion of the substrate the change in the birefringence occurs, and determining the type of particles that is detected based on the portion where the change in the birefringence occurs. The different portions can differ in the dimensions of the structures, the shapes of the structures, the spacing of the structures, or functional layers on the structures.

The method can include placing the sensor in a liquid or gaseous environment that contains target particles to be detected. The method can include coating the sensor with a polymer that contains target particles to be detected. Measuring the birefringence can include measuring an extraordinary index of refraction $n_e$ for a component of the light having a linear polarization parallel to optical axes of the structures, and an ordinary index of refraction $n_o$ for a component of the light having a linear polarization perpendicular to the optical axes of the structures, and determining the birefringence as a difference between the extraordinary index and the ordinary index. The nanostructures can be made of one or more of a metal, a metal oxide, a transition metal oxide, an alloy, a compound, or a polymeric network. The nanostructures can be made of one or more of a dielectric material, a semiconducting material, an electrically insulating material, a ferroelectric material, or a magnetic material. The structures can have functional coatings that interact with the particles.

In general, in another aspect, a method for fabricating a sensor for detecting particles includes providing a substrate, and fabricating a plurality of types of structures on a plurality of regions of a surface of the substrate. The different types of structures are configured to interact with different types of particles, each type of structures being configured to interact with a corresponding type of particles, in which the structures of each region has a birefringence that changes when the structures interact with the corresponding particles.

Implementations of the method may include one or more of the following features. The structures can include nanostructures. The structures can have dimensions ranging from 1 nanometer to 100 micrometers. The structures can include columns, spirals, staircase structures, or chevron structures. Each structure can have a functional layer, and at least two different types of structures have different types of functional layers. The functional layers can include noble metal, aptamer, fibronectin, or antibody. The structures can be fabricated using one or more of a metal, a metal oxide, a transition metal oxide, an alloy, a compound, or a polymeric network to form the structures. The structures can be fabricated using one or more of a dielectric material, a semiconducting material, an electrically insulating material, a ferroelectric material, or a magnetic material to form the structures.

In general, in another aspect, a method for fabricating a sensor for detecting particles includes fabricating structures on a surface of a substrate, and coating the structures with a layer of material to stabilize birefringence of the structures, in which the structures are configured such that the birefringence of the structures with respect to light changes when the structures interact with particles.

Implementations of the method may include one or more of the following features. The structures can include nanostructures. The structures can include one or more of columns, spirals, staircase structures, or chevron structures. The coating material can be inactive to air. The coating material can include one or more of aluminum oxide, titanium oxide, silicon oxide, hafnium oxide, ruthenium oxide, platinum, gold, silver, aluminum, ruthenium, or cobalt. The material can include one or more of a metal, a metal oxide, a transition metal oxide, an alloy, a compound, or a polymeric network. The coating material can include one or more of a dielectric material, a semiconducting material, an electrically insulating material, a ferroelectric material, or a magnetic material.

In general, in another aspect, an apparatus for detecting particles include a substrate; and structures disposed on the substrate in which each of the structures has a functional layer configured to interact with a predetermined type of particles, and the structures have a birefringence that changes when the structures interact with the predetermined type of particles.

Implementations of the apparatus may include one or more of the following features. The structures can include nanostructures. The structures can have dimensions ranging from 1 nanometer to 100 micrometers. The structures can include one or more of columns, spirals, staircase structures, or chevron structures. The structures can include slanted columns that extend along a direction at an angle relative to a surface of the substrate, the angle being less than, e.g., 80 degrees. The structures can be made of a material that reacts with air, and the structures can be coated with thin films that are inactive to air. The material can include cobalt and the thin films can include aluminum oxide. The structures can be coated with a material that includes a metal, a metal oxide, a transition metal oxide, an alloy, a compound, or a polymeric network. The structures can be coated with a material that includes a dielectric material, a semiconducting material, an electrically insulating material, a ferroelectric material, or a magnetic material. The functional layers can include chemical recognition elements or biochemical recognition elements that are configured to interact with the particles. The functional layers can include recognition ligands. The recognition ligands can include at least one of nucleic acid segments, aptamers, peptides, proteins, antibodies, cells, or carbohydrates. The proteins can include fibronectin. The functional layers can be configured to interact with an extracellular matrix of cells. The apparatus can include a light source to emit light that is directed toward the substrate, and a polarization sensitive detector to detect light reflected from the substrate or transmitted through the substrate. The apparatus can include a data processor to process signals from the detector to generate Mueller matrices, and analyze the Mueller matrices to detect changes in the birefringence of the structures. A first portion of the substrate can have structures that interact with the particles, a second portion of the substrate can have structures that do not interact with the particles, the structures in the second portion can have a birefringence that is the same as the birefringence of the structures in the first portion prior to interacting with the particles, and the structures in the second portion can have a birefringence that is different from the birefringence of the structures in the first portion upon interacting with the particles. The substrate can have regions having different types of structures, in which each region has one type of structures, and each type of structures interact with a corresponding type of particles. The different portions can differ in at least one of dimensions of the structures, shapes of the structures, spacing of the structures, or functional layers on the structures. The structures can include at least one of a metal, a metal oxide, a transition metal oxide, an alloy, a compound, or a polymeric network. The structures can include at least one of a dielectric material, a semiconducting material, an electrically insulating material, a ferroelectric material, or a magnetic material. The functional layer can include at least one of aluminum oxide, titanium oxide, silicon oxide, hafnium oxide, ruthenium oxide, platinum, gold, silver, aluminum, ruthenium, or cobalt. The functional layer can include self-assembled monolayers of organic molecules, self-assembled multiple layers of organic molecules, polymer-based surface coatings, oligonucleic acid, or peptide molecules. The functional layer can include a polymer having one or more reactive functional groups, cationic polymer, lipid, or DNA complex.

In general, in another aspect, an apparatus for detecting particles includes a microarray including a substrate having a plurality of regions. Each region has nanostructures configured to interact with a corresponding type of particles, and the nanostructures have a birefringence that changes when the nanostructures interact with corresponding type of particles, and different regions have different nanostructures for detecting different types of particles.

Implementations of the apparatus may include one or more of the following features. The structures can have dimensions ranging from 1 nanometer to 100 micrometers. The nanostructures can include columns, spirals, staircase structures, or chevron structures. The nanostructures can include slanted columns that extend along a direction at an angle relative to a surface of the substrate, the angle being less than 80 degrees. The nanostructures can be made of a material that reacts with air, and the structures can be coated with thin films that are inactive to air. The material of the nanostructures can include cobalt, and the thin films can include aluminum oxide. The nanostructures can have functional layers that include chemical recognition elements or biochemical recognition elements that are configured to interact with the particles. The nanostructures can have functional layers that include at least one of aptamers, peptides, antibodies, fibronectin, or ligands. The nanostructures can have functional layers that are configured to interact with an extracellular matrix of cells. The apparatus can include a light source to emit light that is directed toward the substrate, and a polarization sensitive detector to detect light reflected from the substrate. The apparatus can include a light source to emit light that is directed toward the substrate, and a polarization sensitive detector to detect light transmitted through the substrate. The apparatus can include a data processor to process signals from the detector to generate Mueller matrices, and analyze the Mueller matrices to detect changes in the birefringence of the nanostructures. Each region can have a first portion having structures that interact with the particles and a second portion having structures that do not interact with the particles, the structures in the second portion can have a birefringence that is the same as the birefringence of the structures in the first portion prior to interacting with the particles, and the structures in the second portion can have a birefringence that is different from the birefringence of the structures in the first portion upon interacting with the particles. The nanostructures in the different regions can differ in at least one of dimensions of the structures, shapes of the structures, spacing of the structures, or functional layers on the structures. The nanostructures can include at least one of a metal, a metal oxide, a transition metal oxide, an alloy, a compound, or a polymeric network. The nanostructures can include at least one of a dielectric material, a semiconducting material, an electrically insulating material, a ferroelectric material, or a magnetic material. The nanostructures can have functional layers that include at least one of a metal, a metal oxide, a transition metal oxide, an alloy, a compound, or a polymeric network. The nanostructures can have functional layers that include at least one of a dielectric material, a semiconducting material, an electrically insulating material, a ferroelectric material, or a magnetic material.

The details of one or more of the above aspects and implementations are set forth in the accompanying drawings and the description below. Other features, aspects, and advantages will become apparent from the description, the drawings, and the claims.

DESCRIPTION OF DRAWINGS

FIGS. 1A, 1B, and 1C are diagrams of examples of nanostructures.

FIG. 7A is an image of an array of slanted nanocolumns.

FIG. 7B is an exemplary conoscopic Mueller matrix image.

Like reference symbols in the various drawings indicate like elements.

DETAILED DESCRIPTION

Figure 2A:
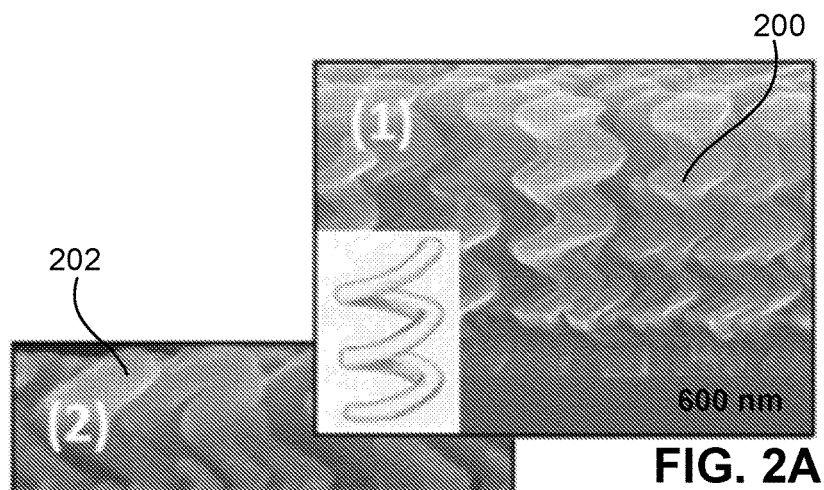
FIGS. 2A, 2B, and 2C are images of examples of nanostructures.

This disclosure provides a novel approach for identifying target materials, including chemical, biochemical, and biological target materials, such as individual small molecules (e.g., molecules in explosives, narcotics, or medicaments), complex molecules (e.g., peptides, deoxyribonucleic acid (DNA), ribonucleic acid (RNA), capsids, or antibodies), and complex biological objects (e.g., cells, parts of cells, or extracellular matrix).

In some implementations, spatially ordered three-dimensional (3D) nanostructures are deposited on surfaces of substrates for sensing and separation of chemical, biochemical, and biological target materials from liquid or gaseous environments. Changes in optical properties, such as birefringence, or optical anisotropy, can be detected by polarization-sensitive linear optical methods, such as ellipsometry or polarimetry, as a function of wavelengths and angle of incidence, in reflection and/or transmission arrangements.

The spatially ordered 3D nanostructures can include, e.g., columns, spirals, staircase structures, or chevron structures. The 3D nanostructures can be fabricated by, for example, glancing angle deposition or non-linear laser polymerization techniques. The 3D nanostructures can be deposited on surfaces such as planar, single crystalline, or amorphous substrates. The 3D nanostructures can have dimensions from a few nanometers to a few micrometers, and can be controlled in their lateral separation and structural form. For example, the spacing between the nanostructures and the pitch of the spirals or staircases can vary depending on applications (e.g., the type of target particles to be identified). The columns can be slanted and extend along a direction at an oblique angle relative to the surface of the substrate.

Referring to FIG. 1A, in some examples, nanostructures 100 can include an array of slanted columns 102, in which one or more sensor molecules such as one or more aptamers 104 are attached to each column 102. In this example, the aptamers 104 can recombine with target DNA segments 106, so the nanostructures 100 can be used to detect the presence of the target DNA segments.

Referring to FIG. 1B, in some examples, nanostructures 110 can include an array of spirals 112 having a shape configured to confine handed (chiral) biological objects, such as capsids 114. In this example, the nanostructures 110 can be used to detect the presence of target capsids.

Referring to FIG. 1C, in some examples, nanostructures 120 can include an array of staircase structures 122. For example, the surface of each staircase structure 122 can be functionalized by a coating 128 that facilitates the capture of complex molecules, such as hepatitis viruses 124. An enlarged portion 126 shows details of the functional coating 128. In this example, the nanostructures 120 can be used to detect the presence of hepatitis viruses.

Referring to FIG. 2A, an array of spiral nanostructures 200 is fabricated on a substrate surface by glancing angle deposition in which particles for building the nanostructures are deposited at an oblique angle relative to the substrate surface, and the substrate is rotated continuously.

Figure 2B:
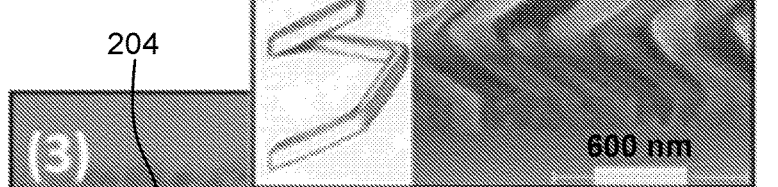

Referring to FIG. 2B, an array of staircase nanostructures 202 is fabricated on a substrate surface by glancing angle deposition in which particles for building the nanostructures are deposited at an oblique angle relative to the substrate surface, and the substrate is rotated discontinuously in a step-wise manner. For example, the substrate is stationary for a brief period of time to allow a first straight segment to be formed, then the substrate is quickly rotated a predetermined number of degrees, and then becomes stationary for a brief period of time to allow a second straight segment to be formed at an angle relative to the first straight segment, and so forth.

Figure 2C:
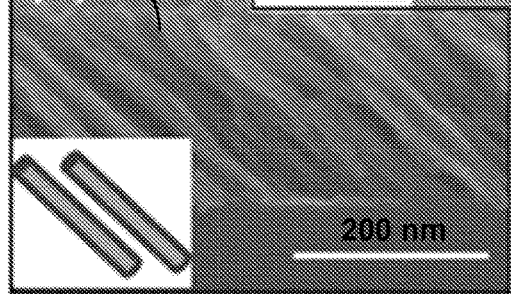

Referring to FIG. 2C, an array of slanted column nanostructures 204 is fabricated on a substrate surface by glancing angle deposition in which particles for building the nanostructures are deposited at an oblique angle relative to the substrate surface, and the substrate is stationary. In the examples of FIGS. 2A to 2C, the materials for building the nanostructures can be, e.g., silicon, cobalt, or other materials.

In some examples, the materials for building the nanostructures can be a metal, a metal oxide, a transition metal oxide, an alloy, a compound, or a polymeric network. The nanostructures made of polymeric networks may be more flexible or bendable than nanostructures made of metals, metal oxides, transition metal oxides, or alloys. In some examples, the materials for building the nanostructures can be a dielectric material, a semiconducting material, an electrically insulating material, a ferroelectric material, or a magnetic material.

Figure 3A:
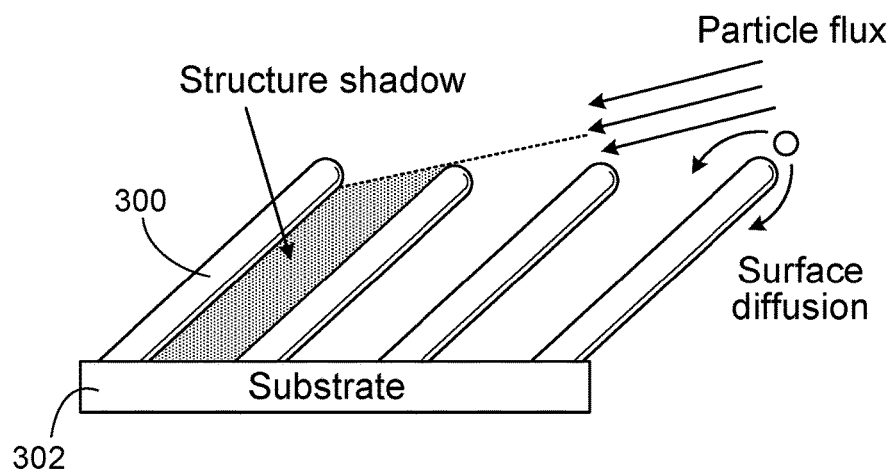
FIGS. 3A and 3B are diagrams showing glancing angle deposition.

Referring to FIG. 3A, glancing angle deposition is used to fabricate slanted nanocolumns 300 on the surface of a substrate 302. In this example, a particle flux is directed at an oblique angle relative to the substrate surface so that the particles are deposited to form slanted columns. Due to the shadowing effect, the particles are not deposited in the spaces between the columns 300.

Figure 3B:
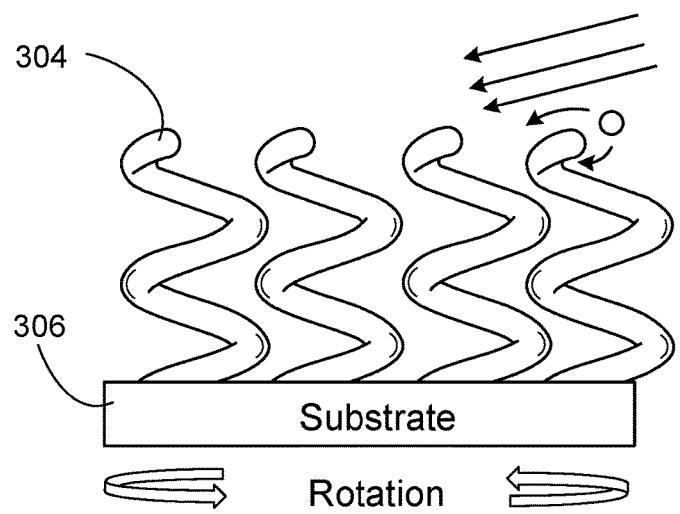

Referring to FIG. 3B, glancing angle deposition is used to fabricate spiral nanostructures 304 on the surface of a substrate 306. In this example, a particle flux is directed at an oblique angle relative to the substrate surface, and the substrate 306 is rotated continuously so that the direction of material buildup changes continuously. Due to the shadowing effect, the particles are not deposited in the spaces between the spirals 304.

The optical properties of the nanostructures can be measured to facilitate detection of target particles. For example, the nanostructures may have a birefringence that varies when the nanostructures interact with particles, such as when the particles come in contact with the nanostructures or when the particles are bound to or captured by the nanostructures. Due to the asymmetric geometry or shape of the nanostructures, the nanostructures may have different ordinary and extraordinary refraction indices resulting in birefringence. In general, the extraordinary index of refraction $n_e$ of a nanostructure refers to the refractive index for a component of light having a linear polarization parallel to an optical axis of the nanostructure, and an ordinary index of refraction $n_o$ of the nanostructure refers to the refractive index for a component of the light having a linear polarization perpendicular to the optical axis of the nanostructure. The birefringence ($\Delta n$) is calculated as a difference between the extraordinary index and the ordinary index, i.e., $\Delta n = n_e - n_o$. For a column, a spiral, or a staircase structure, the optical axis is the center axis of the column, spiral, or staircase structure, respectively.

When the nanostructures interact with particles, there may be changes in the ordinary and extraordinary refractive indices. The nanostructures may interact with particles by, e.g., covalently binding with the particles, non-covalently binding with the particles, or capturing the particles. The amount of change in the ordinary refractive index may be different from the amount of change in the extraordinary refractive index, resulting in a change in the birefringence. Thus, the presence of particles can be detected by detecting changes in the birefringence. For example, a Mueller matrix microscope (M³Scope) image of the nanostructures can be recorded, and changes in the M³Scope image may indicate the presence of the particles.

In this description, when we say "measuring the birefringence of the nanostructures," depending on context it may mean either (i) measuring the birefringence of the nanostructures without target particles being attached to the nanostructures, or (ii) measuring the birefringence of the nanostructures with the target particles attached to the nanostructures. In some examples, the target particles may affect the polarization states of light (e.g., the target particles may have dipoles), and "measuring the birefringence of the nanostructures" may mean measuring the birefringence due to the cumulative effects of the nanostructures and the target particles attached to the nanostructures.

FIGS. 2A to 2C show examples of nanostructures that may exhibit changes in birefringence upon interaction with particles. Other types of spatially ordered 3D nanostructures can also be used. The spatially ordered 3D nanostructures can have highly coherent shapes (e.g., they can be similar in structure, dimension, physical appearance, and material), and can be arranged with respect to each other in an ordered manner. The locations of the individual nanostructures on the substrate surface can be random or ordered. The density of the nanostructures on the substrate surface can be constant or vary across the substrate surface.

In some implementations, in order to generate a meaningful detection signal, it is preferable to have an array of several nanostructures that are highly spatially ordered. The nanostructures are probed by light having a wavelength that is larger than the dimension of the nanostructure. By having several nanostructures that behave in the same manner arranged within a region having dimensions of a couple of wavelengths, a stronger signal may be detected.

The nanostructures can be designed to be sensitive to a specific target molecule. For example, the distances between columns or spirals, or the widths or diameters of the structures, can be selected to match the dimensions of the target molecules such that the target molecules can easily attach to the nanostructures.

The spatially ordered 3D nanostructures can detect the presence of chemical, biochemical, and biological target materials upon exposing the nanostructures to environments that carry such target material. For example, the target material can be diffused in a gaseous environment or dissolved in a liquid environment. The optical properties of the spatially ordered 3D nanostructures are modified upon interaction with the chemical, biochemical, and biological target materials. Changes in the optical properties can include, e.g., variations of the birefringence, or optical anisotropy, of the nanostructures. The changes in the birefringence can be detected by polarization-sensitive linear optical methods, such as ellipsometry or polarimetry, as a function of wavelengths and angle of incidence, in reflection and/or transmission arrangements. The detection of variations in the birefringence can be performed for a range of the electromagnetic spectrum using wavelengths from the upper gigahertz range to the vacuum ultra violet region.

The spatially ordered 3D nanostructures may be functionalized by modifying their surfaces, e.g., by attaching additional chemical and biochemical recognition ligands, e.g., DNA segments, aptamers, peptides, proteins (e.g., fibronectin), antibodies, cells, or carbohydrates (e.g., lectins) to the surfaces of the spatially ordered 3D nanostructures by linker chemistry. FIG. 1C shows an example of a nanostructure that is functionalized by the coating 128.

The surfaces of the spatially ordered 3D nanostructures can be modified by, e.g., chemical and vapor deposition, or liquid solvent based deposition. The purposes of the modifications are to (a) vary the chemical surface potential for subsequent attachment of chemical linker elements such as self-assembled monolayers consisting of organic molecules, and (b) facilitate attachment of specific sensor molecules to the surface such as aptamers or proteins.

The shape or structure of the three-dimensional nanostructure provides the ability to change birefringence when a target particle attaches to it. The functionalization makes the nanostructure specific so that only a specific type of target particle will interact or attach to the nanostructure, or a specific type of target particle will cause configuration change of an already attached molecule. The combination of the structure and functional coating of the three-dimensional nanostructure enables detection of a specific type of target particle based on changes in birefringence.

In some examples, a sensor having column, chevron, and/or staircase nanostructures can be configured to detect target particles that include nanoparticles of elements, alloys, or compounds, or complex structured nanoparticles. The nanostructures can either be with or without functional coatings. The functional coatings can be, e.g., aluminum oxide, titanium oxide, silicon oxide, hafnium oxide, ruthenium oxide, platinum, gold, silver, aluminum, ruthenium, and/or cobalt.

In some examples, a sensor having column, chevron, spiral, or staircase nanostructures can be configured to detect elemental or molecular gas target particles. The nanostructures can be either with or without functional coatings. The functional coatings can include, e.g., aluminum oxide, titanium oxide, silicon oxide, hafnium oxide, ruthenium oxide, platinum, gold, silver, aluminum, ruthenium, and/or cobalt. The functional coatings can include, e.g., self-assembled monolayers of organic molecules, self-assembled bi-layers of organic molecules, self-assembled multiple layers of organic molecules, polymer-based surface coatings, oligonucleic acid that bind to a specific target element or molecule (aptamer), and/or peptide molecules that bind to a specific target element or molecule (aptamer).

In some examples, a sensor having column, chevron, and/or staircase nanostructures can be configured to detect DNA and/or RNA segments. The nanostructures can be either with or without functional coatings. The functional coatings can include, e.g., aluminum oxide, titanium oxide, silicon oxide, hafnium oxide, ruthenium oxide, platinum, gold, silver, aluminum, ruthenium, and/or cobalt. The functional coatings can include, e.g., self-assembled monolayers of organic molecules, self-assembled bi-layers of organic molecules, self-assembled multiple layers of organic molecules, polymer-based surface coatings, oligonucleic acid that bind to a specific target element or molecule (aptamer), and/or peptide molecules that bind to a specific target element or molecule (aptamer).

In some examples, a sensor having column, chevron, and/or staircase nanostructures can be configured to detect small molecule peptides, e.g., cocaine. The nanostructures can be either with or without functional coatings. The functional coatings can be, e.g., aluminum oxide, titanium oxide, silicon oxide, hafnium oxide, ruthenium oxide, platinum, gold, silver, aluminum, ruthenium, and/or cobalt. The functional coatings can be, e.g., self-assembled monolayers of organic molecules, self-assembled bi-layers of organic molecules, self-assembled multiple layers of organic molecules, polymer-based surface coatings, oligonucleic acid that bind to a specific target element or molecule (aptamer), and/or peptide molecules that bind to a specific target element or molecule (aptamer).

In some examples, a sensor having spiral and/or staircase nanostructures can be configured to detect steric molecules. The nanostructures can be either with or without functional coatings. The functional coatings can include, e.g., aluminum oxide, titanium oxide, silicon oxide, hafnium oxide, ruthenium oxide, platinum, gold, silver, aluminum, ruthenium, and/or cobalt. The functional coatings can include, e.g., self-assembled monolayers of organic molecules, self-assembled bi-layers of organic molecules, self-assembled multiple layers of organic molecules, polymer-based surface coatings, oligonucleic acid that bind to a specific target element or molecule (aptamer), and/or peptide molecules that bind to a specific target element or molecule (aptamer).

In some examples, a sensor having spiral and/or staircase nanostructures can be configured to detect capsids or viruses. The nanostructures can be either with or without functional coatings. The functional coatings can include, e.g., aluminum oxide, titanium oxide, silicon oxide, hafnium oxide, ruthenium oxide, platinum, gold, silver, aluminum, ruthenium, and/or cobalt. The functional coatings can include, e.g., self-assembled monolayers of organic molecules, self-assembled bi-layers of organic molecules, self-assembled multiple layers of organic molecules, polymer-based surface coatings, oligonucleic acid that bind to a specific target element or molecule (aptamer), and/or peptide molecules that bind to a specific target element or molecule (aptamer).

In some examples, a sensor having column, chevron, spiral and/or staircase nanostructures can be configured to detect antibodies. The nanostructures can be either with or without functional coatings. The functional coatings can include, e.g., aluminum oxide, titanium oxide, silicon oxide, hafnium oxide, ruthenium oxide, platinum, gold, silver, aluminum, ruthenium, and/or cobalt. The functional coatings can include, e.g., self-assembled monolayers of organic molecules, self-assembled bi-layers of organic molecules, self-assembled multiple layers of organic molecules, polymer-based surface coatings, oligonucleic acid that bind to a specific target element or molecule (aptamer), and/or peptide molecules that bind to a specific target element or molecule (aptamer). The functional coatings can include, e.g., polymers having reactive functional groups, and/or protein for direct immobilization of virus-specific antibodies.

In some examples, a sensor having column, chevron, spiral and/or staircase nanostructures can be configured to detect cells. The nanostructures can be either with or without functional coatings. The functional coatings can include, e.g., aluminum oxide, titanium oxide, silicon oxide, hafnium oxide, ruthenium oxide, platinum, gold, silver, aluminum, ruthenium, and/or cobalt. The functional coatings can include, e.g., self-assembled monolayers of organic molecules, self-assembled bi-layers of organic molecules, self-assembled multiple layers of organic molecules, polymer-based surface coatings, oligonucleic acid that bind to a specific target element or molecule (aptamer), and/or peptide molecules that bind to a specific target element or molecule (aptamer). The functional coatings can include, e.g., polymers having reactive functional groups, and/or protein for direct immobilization of virus-specific antibodies. The functional coatings can include, e.g., structures of cationic polymer, structures of lipid, and/or DNA complex having high concentration of certain DNA.

Figure 4:
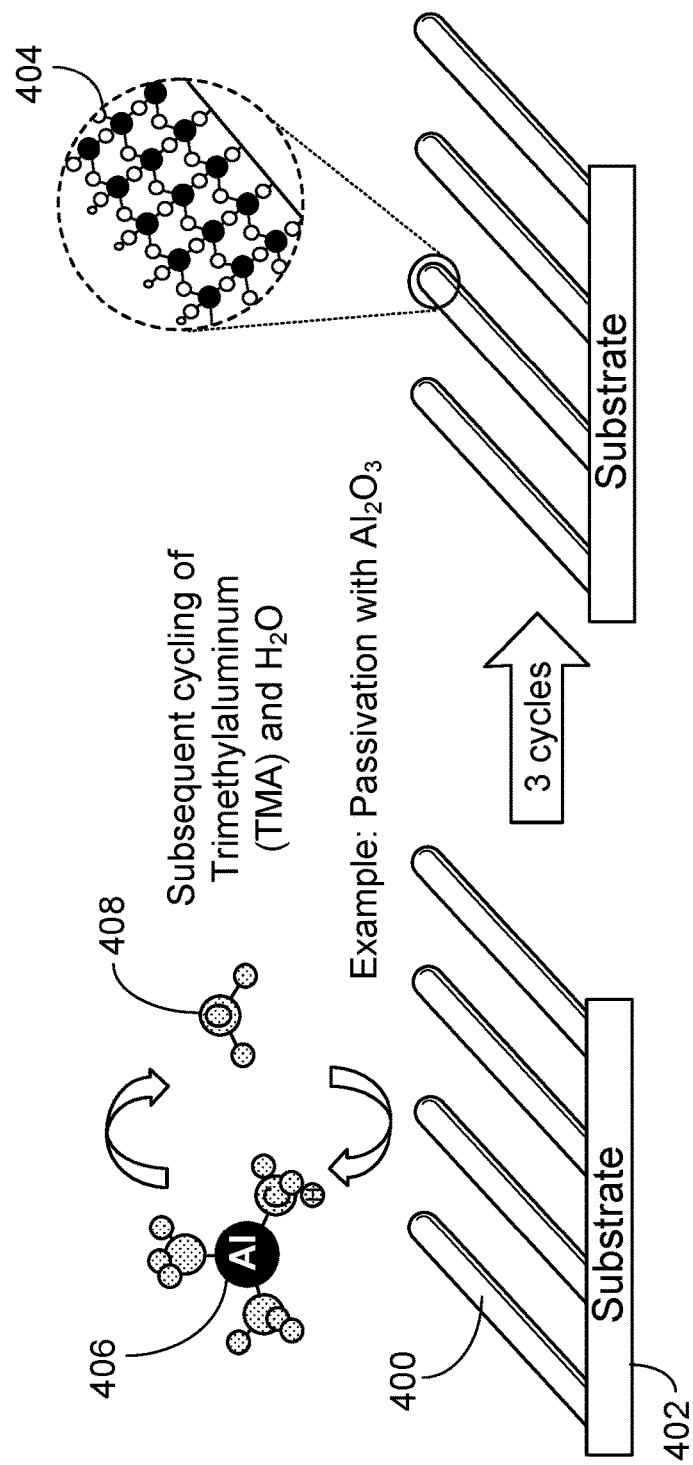
FIG. 4 is a diagram showing atomic layer deposition.

Referring to FIG. 4, in some implementations, atomic layer deposition can be used for uniform, monolayer coating of spatially ordered 3D nanostructures deposited on surfaces. The coherent deposition of thin films can modify the surface properties of the nanostructures. In this example, an array of slanted column nanostructures 400 is fabricated on the surface of a substrate 402, and a layer of aluminum oxide ($Al_2O_3$) 404 is formed on the surface of the columns 400 by atomic layer deposition using $Al(CH_3)$ (trimethylaluminum (TMA)) 406 and water ($H_2O$) 408 as the reactants. Three cycles of depositions using TMA and $H_2O$ were used to form three layers of aluminum oxide 404 on each of the columns 400.

An advantage of coating the nanostructures with aluminum oxide is that aluminum oxide is stable in the air. Passivation of the nanostructures allows the nanostructures to remain stable in air even if the material (e.g., cobalt) for constructing the nanostructures is reactive to air. This allows the optical properties, such as birefringence, of the passivated nanostructures to remain stable over time.

Figure 5:
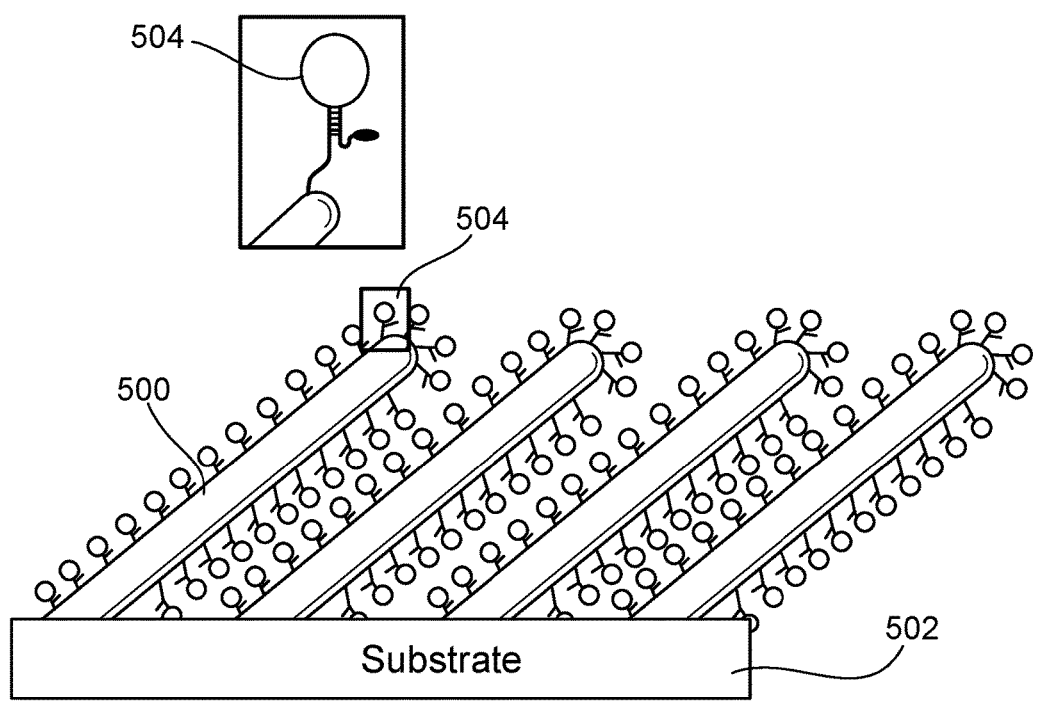
FIG. 5 is a diagram of examples of nanostructures each having a monolayer of aptamers.

Referring to FIG. 5, in some implementations, slanted columns 500 are formed on the surface of a substrate 502. A monolayer of aptamers 504 is formed on the surface of each column 500 to facilitate DNA or RNA sensing.

In some implementations, the method of detecting particles based on detecting changes in the birefringence of the nanostructures can be applied in-situ while the probing electromagnetic radiation traverses the environment containing the target material. In some implementations, the probing electromagnetic radiation traverses through the backside of the substrate and is reflected by the front side that has the nanostructures, in which the reflected electromagnetic radiation being analyzed does not traverse the target containing environment. This is useful when, e.g., the environment is not transparent to the probing electromagnetic radiation.

A sensor having spatially ordered 3D nanostructures can be designed such that the nanostructures are deposited on a small region of a substrate surface, in which the dimension of the small region can be on the order of the wavelength of the probing electromagnetic radiation. When the sensor is deployed to detect particles, a probing electromagnetic radiation can be focused by optical elements to reduce the size of the probing area on the substrate surface.

The optical focusing scheme allows for the miniaturization of the region needed for sensing a particular kind of particle. The surface of the substrate can have several regions having different spatially ordered 3D nanostructures of various geometries and/or various surface functional layers to form an array of sensing elements. The various regions (or sensing elements) can be read out by, e.g., polarization-sensitive optical imaging methods, such as ellipsometry or polarimetry imaging.

Figure 6:
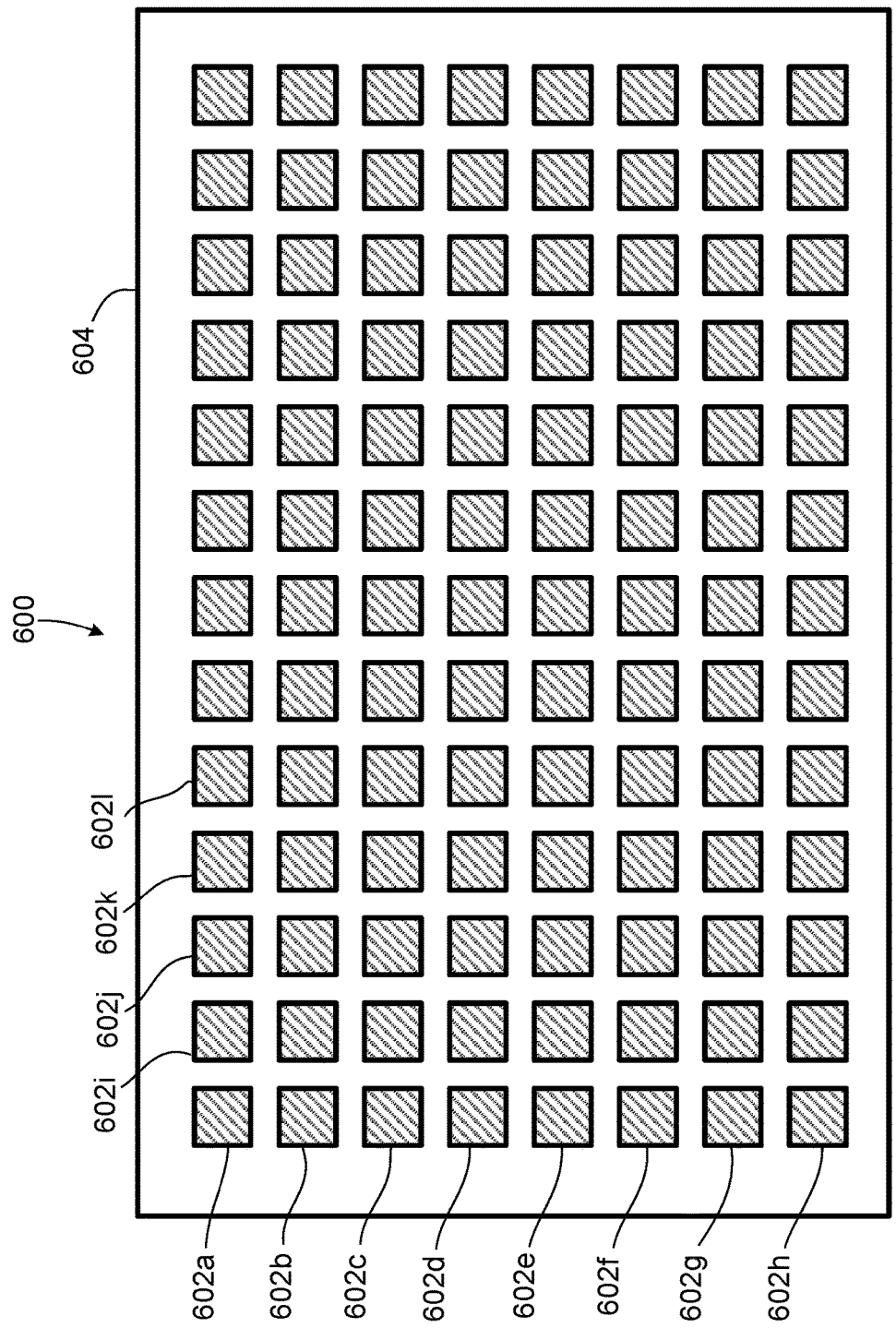
FIG. 6 is a diagram of an exemplary microarray.

Referring to FIG. 6, in some implementations, a microarray 600 includes a substrate 604 on which spatially ordered 3D nanostructures are formed. The microarray 600 includes regions, e.g., 602a, 602b, 602c, . . . , 602l, collectively referenced as 602, that have spatially ordered 3D nanostructures in which different regions are configured to detect different particles. In some implementations, the different regions may have different types of nanostructures. For example, region 602a may have an array of spiral nanostructures, region 602b may have an array of spiral staircases, and region 602c may have an array of slanted columns.

In some implementations, different regions may have the same type of nanostructures in which the nanostructures have different dimensions. For example, regions 602e and 602f may both have arrays of spiral nanostructures, in which the pitch and/or diameter of the spirals in the region 602e is different from the pitch and/or diameter of the spirals in the region 602f. For example, regions 602g and 602h may both have arrays of slanted columns, in which the incline angle of the columns in the region 602g is different from the incline angle of the columns in the region 602h.

In some implementations, the nanostructures of different regions may have different functional coatings. For example, regions 602i and 602j may have nanostructures in which a first type of aptamers are attached to the nanostructures in the region 602i and a second type of aptamers are attached to the nanostructures in the region 602j. The region 602i may be used to detect a first type of DNA segment and the region 602j may be used to detect a second type of DNA segment. For example, regions 602k and 602l may have nanostructures in which the nanostructures in the region 602k are coated with a first functional layer and the nanostructures in the region 602l are coated with a second functional layer. The region 602k may be used to detect a first type of capsid and the region 602l may be used to detect a second type of capsid.

In some implementations, sensing of target particles is performed by readout of the polarization state changes that indicate interaction with or attachment of target objects to the nanostructures. In some implementations, the nanostructures can bind to the target objects and selectively remove the target objects from the environment to which the nanostructures are exposed.

The interaction (e.g., attachment) of chemical and biochemical target particles to the nanostructures can be detected using optical methods. For example, visible light ellipsometry can be used to measure changes in birefringence of nanostructures to detect fibronectin in slanted columnar spatially ordered three-dimensional nanostructures deposited on surfaces. Angle-of-incidence resolved single-wavelength and spectroscopic generalized ellipsometry measurements, such as $M^3$Scope analysis, can be performed to measure changes in birefringence of spatially ordered three-dimensional nanostructures deposited on surfaces. For example, terahertz radiation can be used to measure the dielectric anisotropy of metal slanted columnar thin films.

Referring to FIG. 7A, an array of cobalt slanted column nanostructures 610 are fabricated on the surface of a substrate 612. The cobalt slanted nanostructures 610 are coated with $Al_2O_3$ by atomic layer deposition in which the $Al_2O_3$ layer has a thickness of about 4 nm.

Referring to FIG. 7B, ellipsometric analysis of the cobalt slanted nanostructure coated with $Al_2O_3$ was performed to produce an $M^3$Scope image 614 that reveals structural and dielectric information (e.g., thickness of coating layer, slanting angle, column diameter, filling factor, and dielectric anisotropy). Although the image 614 in FIG. 7B is shown in gray-scale, the original image can be in color. The $M^3$Scope measurements provide an angular-resolved (conoscopic) image of the Mueller matrix elements representing the optical properties of the spatially ordered three-dimensional nanostructures. The off-diagonal block elements of the Mueller matrix data contain information about the birefringence of the spatially ordered three-dimensional nanostructures.

Figure 8A:
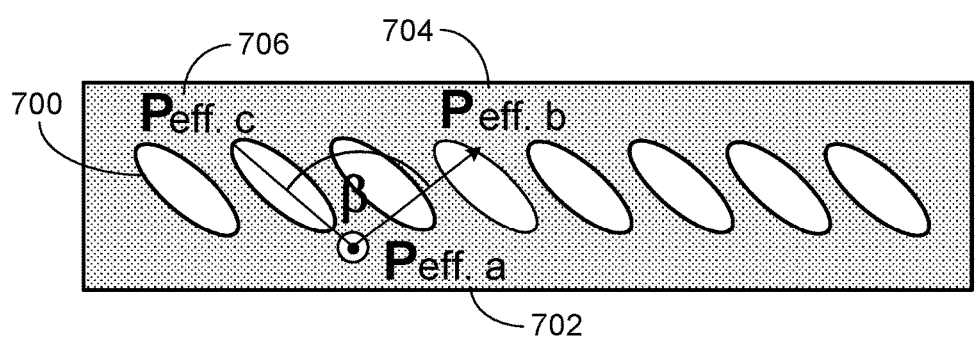
FIG. 8A is a diagram of exemplary slanted nanocolumns.

Referring to FIG. 8A, a slanted nanocolumn 700 has anisotropic polarization vectors Peff,a 702, Peff,b 704, and Peff,c 706. The polarization vectors represent the effective polarizabilities and produce the anisotropic dielectric function tensor of the spatially ordered 3D nanocolumns.

Figure 8B:
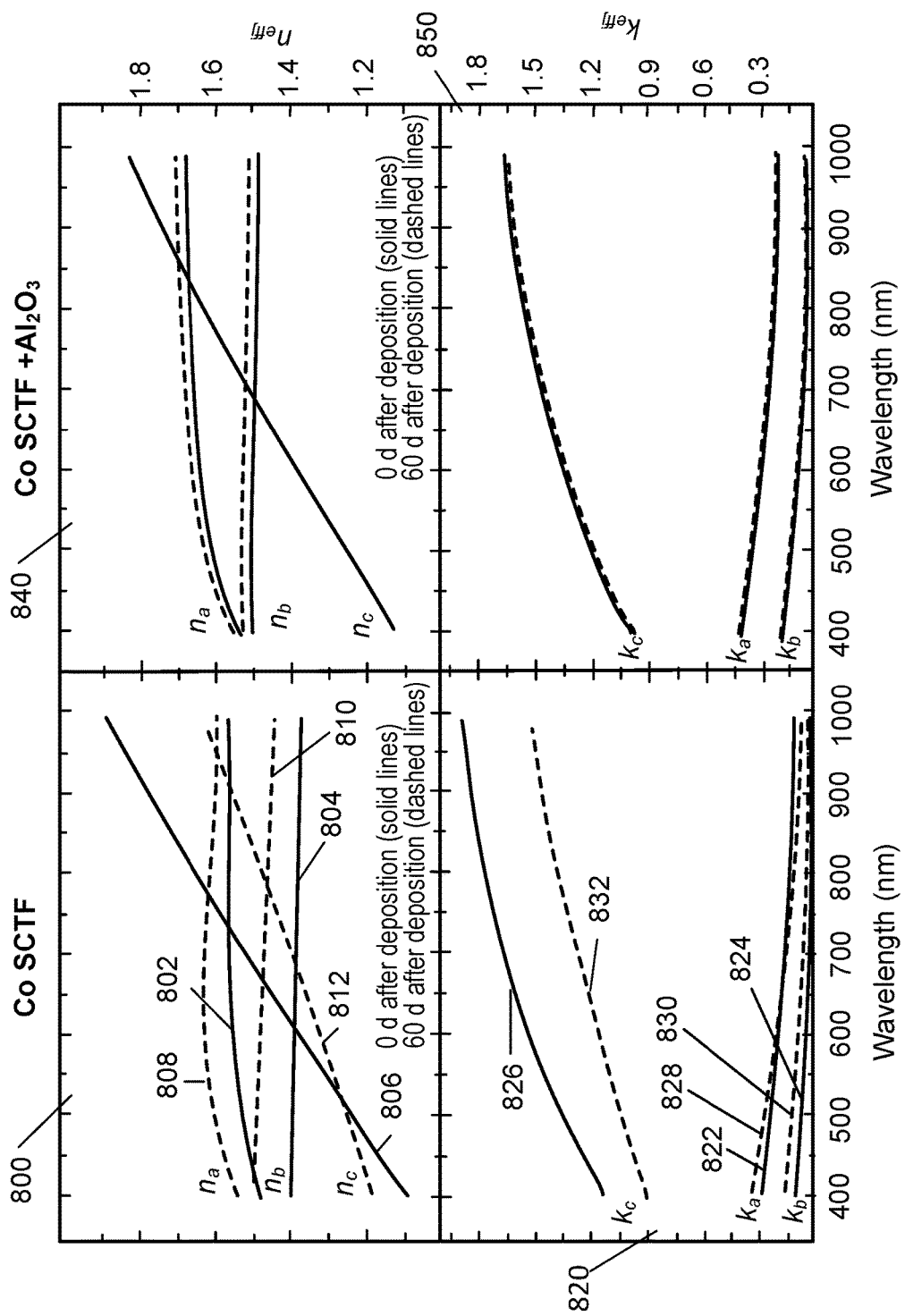
FIG. 8B show graphs representing exemplary refraction coefficients and extinction coefficients as functions of wavelength.

Referring to FIG. 8B, a graph 800 shows anisotropic indices or refraction coefficients determined from the $M^3$Scope analysis for a sculptured thin film (STF) having cobalt slanted nanocolumns. Part of the sculptured thin film was exposed to normal ambient, and upon oxidation the optical constants of the sculptured thin film changed after 60 days. Solid lines 802, 804, and 806 represent the refractive indices $n_a$, $n_b$, and $n_c$ measured along polarization directions a, b, c, respectively, as indicated in FIG. 7, of the slanted nanocolumns immediately after deposition of the nanocolumns for a range of wavelengths. Dashed lines 808, 810, and 812 represent the refractive indices $n_a$, $n_b$, and $n_c$, respectively, of the slanted nanocolumns 60 days after the deposition of the nanocolumns measured over a range of wavelengths. A comparison of the solid and dashed lines in the graph 800 shows that cobalt oxidation affected the optical constants after 60 days for the uncoated part of the sample.

A graph 820 shows extinction coefficients determined from the M³Scope analysis for the cobalt slanted nanocolumns. Solid lines 822, 824, and 826 represent the extinction coefficients $k_a$, $k_b$, and $k_c$, respectively, of the slanted nanocolumns immediately after deposition of the nanocolumns measured over a range of wavelengths. Dashed lines 828, 830, and 832 represent the extinction coefficients $k_a$, $k_b$, and $k_c$, respectively, of the slanted nanocolumns 60 days after the deposition of the nanocolumns. A comparison of the solid and dashed lines in the graph 820 also shows that cobalt oxidation affected the optical constants after 60 days for the uncoated part of the sample.

The other part of the sculptured thin film was coated with 4 nm $Al_2O_3$ by atomic layer deposition immediately after growth of the nanocolumns by glancing angle deposition to prevent oxidation. In a graph 840, solid lines represent the refractive indices $n_a$, $n_b$, and $n_c$, respectively, of the slanted $Al_2O_3$ coated nanocolumns immediately after deposition of the nanocolumns measured over a range of wavelengths. Dashed lines represent the refractive indices $n_a$, $n_b$, and $n_c$, respectively, of the slanted $Al_2O_3$ coated nanocolumns 60 days after the deposition of the nanocolumns measured over a range of wavelengths. In a graph 850, solid lines represent the extinction coefficients $k_a$, $k_b$, and $k_c$, respectively, of the slanted $Al_2O_3$ coated nanocolumns immediately after deposition of the nanocolumns measured over a range of wavelengths. Dashed lines represent the extinction coefficients $k_a$, $k_b$, and $k_c$, respectively, of the slanted $Al_2O_3$ coated nanocolumns 60 days after the deposition of the nanocolumns. Comparisons of the solid and dashed lines in graphs 840 and 850 show little or no change of the optical constants for a range of wavelengths over the 60-day period. This indicates that the $Al_2O_3$ coated nanocolumns can remain stable over a long period of time and be useful in detecting target particles.

In some implementations, the nanostructures can be hybridized with a polymer. For example, a layer of polymer can be applied over an array of nanocolumns such that the polymer covers the nanocolumns and fills the spaces between the nanocolumns. For example, titanium chevron nanostructures can be hybridized with a semiconducting polymer P3DDT (Poly(3-dodecylthiophene)). The infiltration of the polymer within the nanostructures results in substantial changes of their optical constants, and therefore in their polarization response to a polarized light beam.

In some examples, a sensor that includes nanostructures immersed in a polymer may be placed in an environment to detect target particles in the environment. The target particles may diffuse through the polymer and interact with (e.g., attach to) the nanostructures and change the optical properties, such as birefringence, of the nanostructures. In some examples, the polymer may include target particles such that when the polymer is applied over the nanostructures, the target particles diffuse through the polymer and interact with (e.g., attach to) the nanostructures and change the optical properties, such as birefringence, of the nanostructures.

Figure 9:
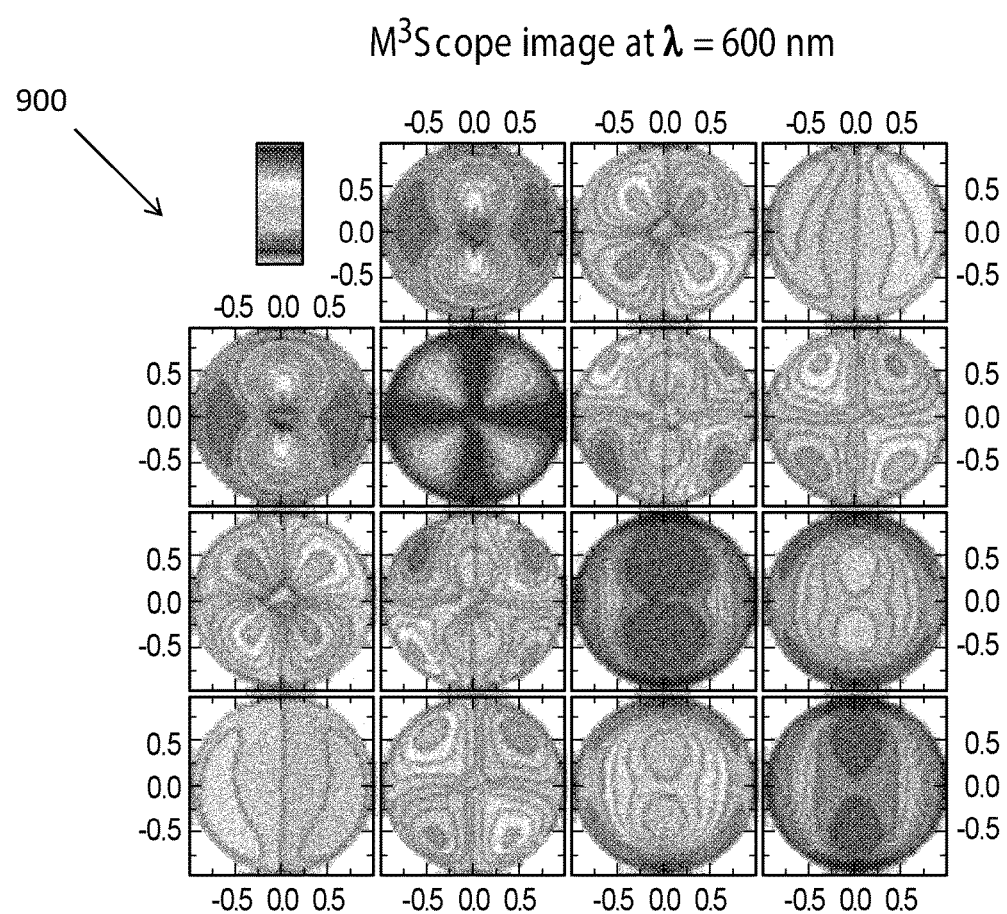
FIG. 9 is an exemplary conoscopic Mueller image.

Referring to FIG. 9, an in-situ M³Scope analysis was performed to quantify the attachment of fibronectin in pore volume between nanocolumns. The slanted cobalt columnar nanostructures 610 coated with 4 nm $Al_2O_3$ (see FIG. 7A) was immersed in a diluted solution of fibronectin (1× diluted phosphate buffered saline (PBS) with fibronectin 50 microgram per millimeter), causing the fibronectin to be attached to the slanted columnar nanostructures. An in-situ ellipsometric analysis was performed on the sample to generate an M³Scope image 900, which reveals incorporation of the fibronectin within 10% of the space between the nanocolumns. The information is obtained from the changes of the off-diagonal blocks of the Mueller matrix data detected with generalized ellipsometry measurements.

A comparison of the M³Scope image 900 in FIG. 9 and the M³Scope image 614 in FIG. 7B shows differences in the off-diagonal blocks of the Mueller matrix. The off-diagonal block elements of the Mueller matrix vary upon incorporation of organic materials within the spatially ordered three-dimensional nanostructures. The changes in the Mueller matrix data may be caused by, e.g., changes in the birefringence within the nanostructures. The changes in birefringence may be caused by, e.g., the screening of the dipole polarizabilities of the spatially ordered three-dimensional nanostructures by the molecular dipoles of the target objects brought within the nanostructures.

Figure 10:
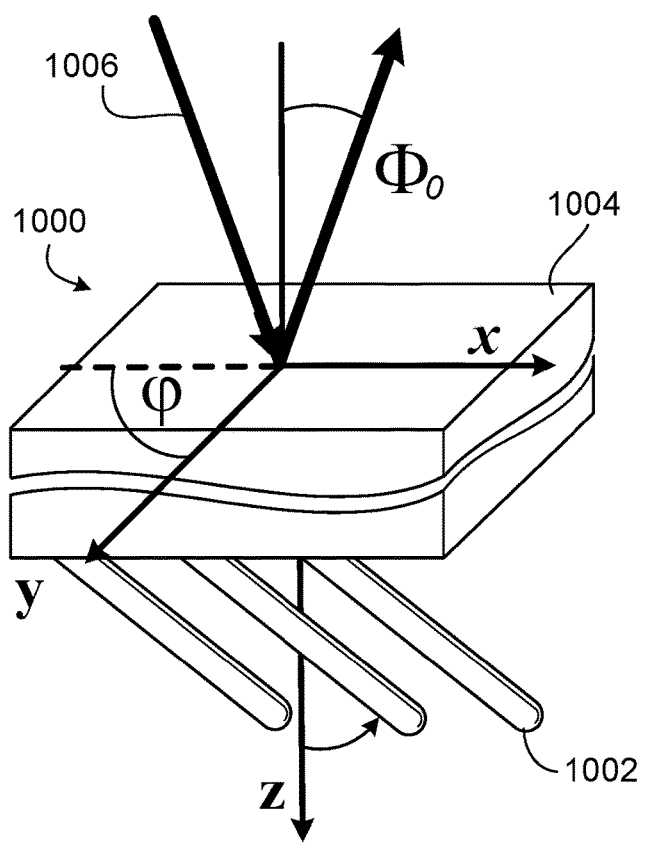
FIG. 10 is a diagram showing an exemplary setup for detecting target particles in a liquid.

Referring to FIG. 10, terahertz spectroscopic generalized ellipsometry can be used to detect infiltration of a dielectric liquid into slanted columnar nanostructures. A sensor 1000 includes an array of nanocolumns 1002 formed on an undoped silicon wafer 1004, which is transparent to terahertz radiation. The sensor 1000 can be partially immersed in dielectric water in a flow cell and oriented such that the nanocolumns 1002 are immersed in the dielectric water. The measurements can be performed in which terahertz radiation 1006 is directed toward the silicon wafer 1004 from the backside of the wafer 1004 (i.e., the side that does not have the nanocolumns). The ellipsometric beam 1006 was not guided through the dielectric water. This way of measuring changes in the birefringence of nanostructures is useful when, e.g., the target molecules are in a solvent or ambient that is not transparent to the probe beam. For example, infrared radiation does not transmit well in water. Because the radiation does not travel through the non-transparent ambient environment, signal degradation can be reduced.

Figure 11:
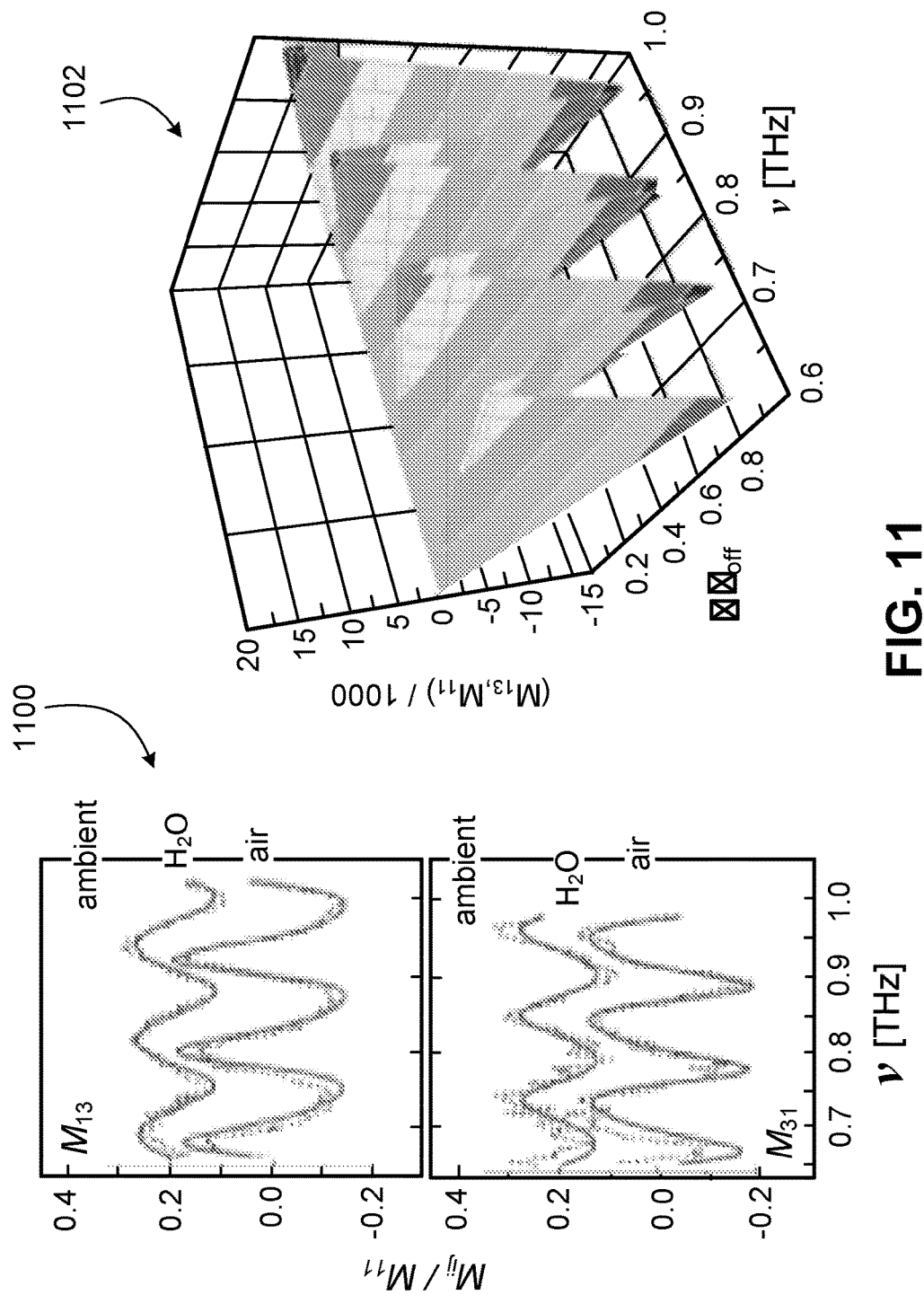
FIG. 11 shows graphs representing exemplary results of ellipsometry measurements.

Referring to FIG. 11, ellipsometry measurements were performed by immersing nanocolumns in ultra-pure water. A graph 1100 shows measurements from the off-diagonal block Mueller matrix elements as a function of wavelengths, which indicate strong signal variations upon exposure of the nanostructures to water. A graph 1102 shows simulated terahertz ellipsometry data from slanted cobalt nanocolumns immersed in a liquid as a function of the liquid's polarity (dielectric polarizability), deviating from ultra-pure water ($de_{off}$). The simulations demonstrate that this optical method can have a large sensitivity to the dielectric polarizability of the incorporated liquid. The simulations and experiments show that attachment of organic target molecules can be detected through the transparent substrates onto which the spatially ordered three-dimensional nanostructures are deposited.

The ellipsometry measurements for detecting changes in the birefringence of the nanostructures can be performed in several ways.

Figure 12:
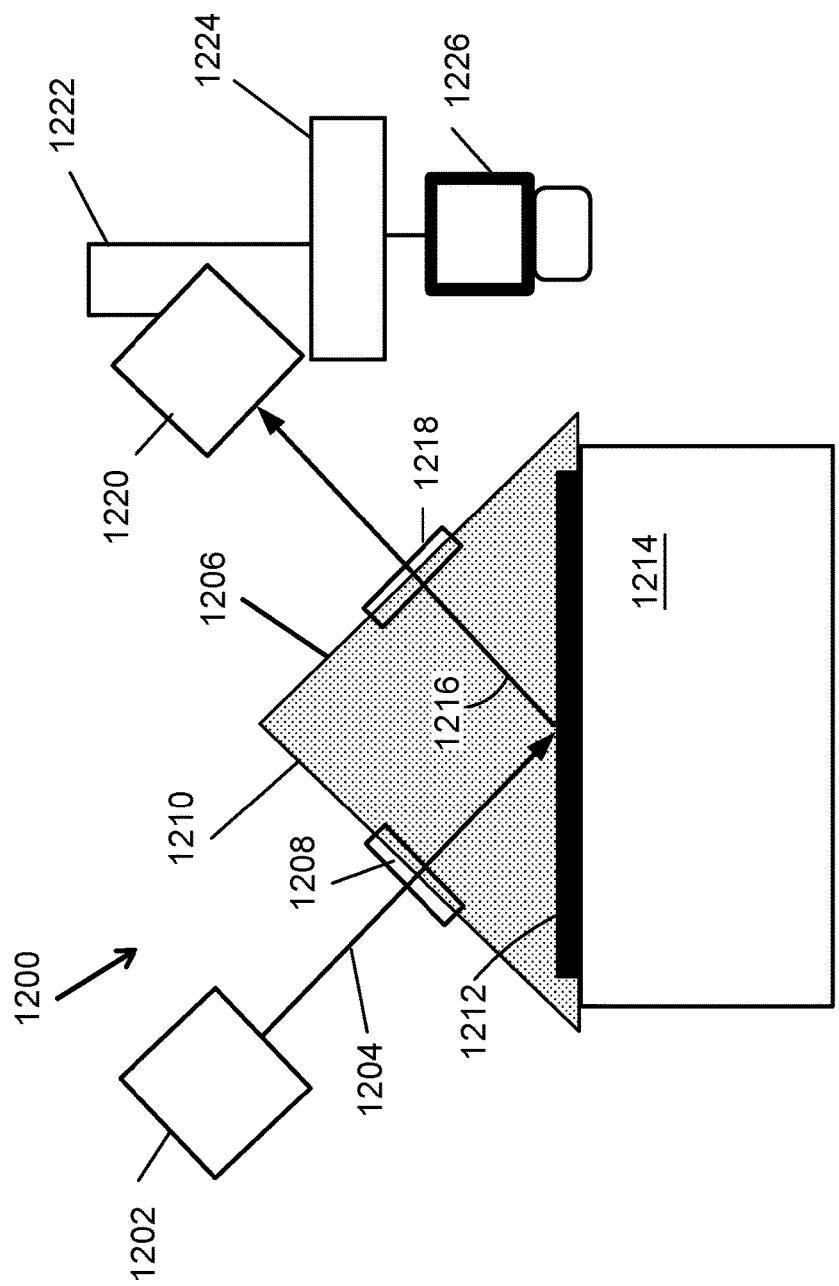
FIG. 12 is a diagram of an exemplary reflection-type in-situ detection system.

Referring to FIG. 12, in some implementations, a reflection-type in-situ detection system 1200 can be used to detect target particles. Spatially ordered three-dimensional nanostructures formed on a substrate are exposed to a gaseous or liquid environment within a cell, in which the environment carries target materials. The nanostructures are investigated by a polarized optical light beam through windows of the cell.

The detection system 1200 includes an optical system 1202 that produces a collimated polarized light beam 1204, which enters a cell 1206 through a window 1208. The cell 1206 encloses an environment 1210 (a gaseous atmosphere or a liquid solution) that carries target objects. The light beam 1204 interacts with nanostructures 1212 attached to the surface of a substrate 1214. The reflected light beam 1216 exits the cell 1206 through a window 1218 and is analyzed by a polarization sensitive instrument 1220 (e.g., ellipsometer) for its polarization state. The polarization state information is transmitted through an interconnect 1222 to a computer 1224 that processes the information. The computer 1224 may provide a graphical representation of the information, e.g., an $M^3$Scope image that can be shown on a display 1226 or stored in a data storage device. When the measurements show changes in the birefringence of the nanostructures, it may indicate detection of target particles.

Figure 13:
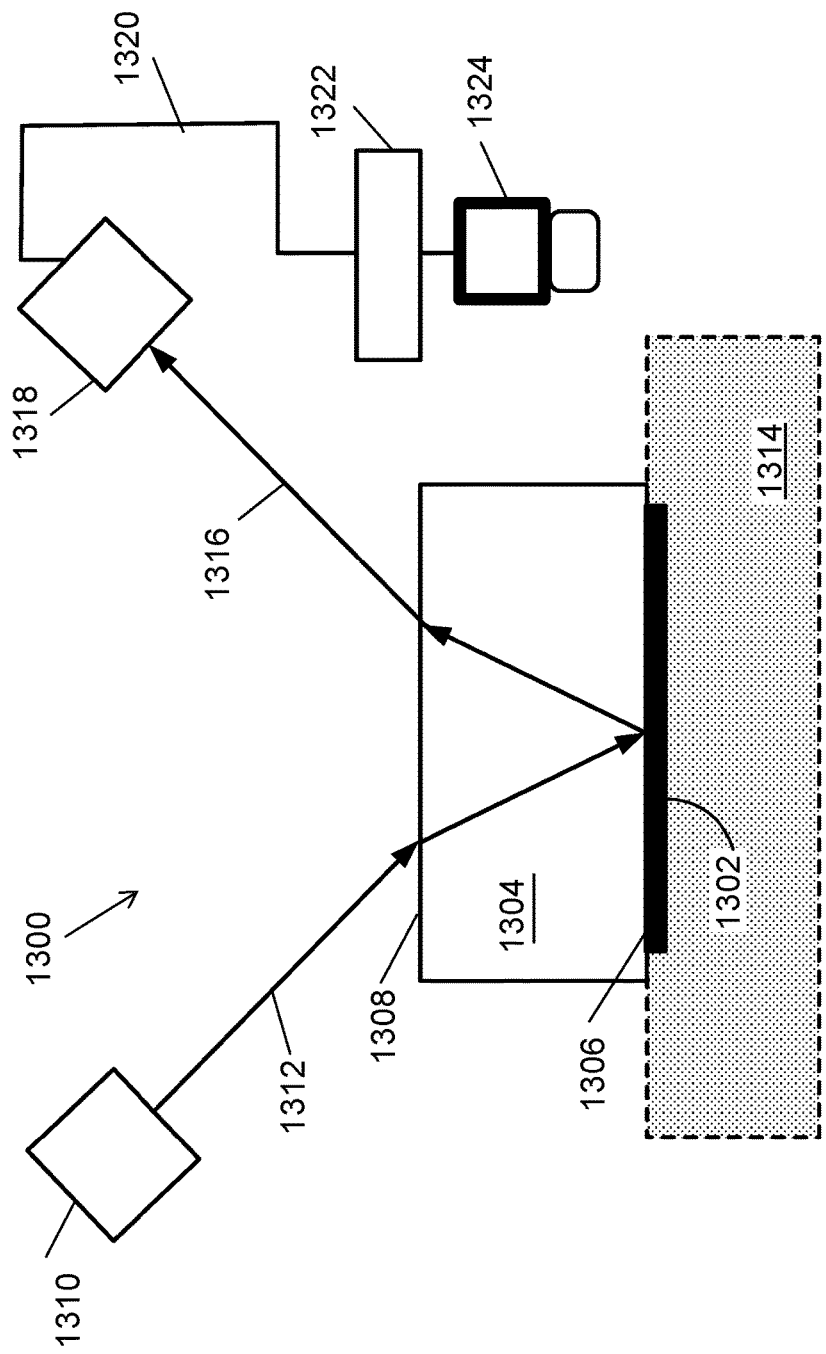
FIG. 13 is a diagram of an exemplary transmission-type in-situ detection system.

Referring to FIG. 13, in some implementations, a transmission-type in-situ detection system 1300 can be used to detect target particles. The spatially ordered three-dimensional nanostructures are exposed to an environment carrying target materials and investigated by a polarized optical light beam through the back side of the substrate that carries the nanostructures. The substrate is selected to be transparent for the wavelengths of the polarized probing light beam. The probing light does not traverse the environment to which the nanostructures are exposed.

In some examples, spatially ordered three-dimensional nanostructures 1302 are formed on a substrate 1304. For example, the substrate 1304 can have a front side 1306 and a back side 1308 that are parallel to each other. In this example, the front side 1306 refers to the side where the nanostructures 1302 are formed. An optical system 1310 produces a collimated polarized light beam 1312 that approaches the back side 1308 of the substrate 1304 at an oblique angle and refracts through the back side 1308 towards the front side 1306 that carries the nanostructures 1302. The nanostructures 1302 are exposed to an environment 1314 (e.g., fluid or gaseous) that may contain target materials. The light interacts with the nanostructures 1302 and is reflected back towards the back side 1308. The reflected light 1316 exits the back side 1308 of the substrate 1304 and is analyzed by a polarization sensitive instrument 1318 for its polarization state. The polarization state information is transmitted through an interconnect 1320 to a computer 1322 that processes the information. The computer 1322 may provide a graphical representation of the information, e.g., an $M^3$Scope image that can be shown on a display 1324 or stored in a data storage device. When the measurements show changes in the birefringence of the nanostructures, it may indicate detection of target particles. The system 1300 is called a "transmission-type" system because the probe light is transmitted through the substrate 1304.

Figure 14A:
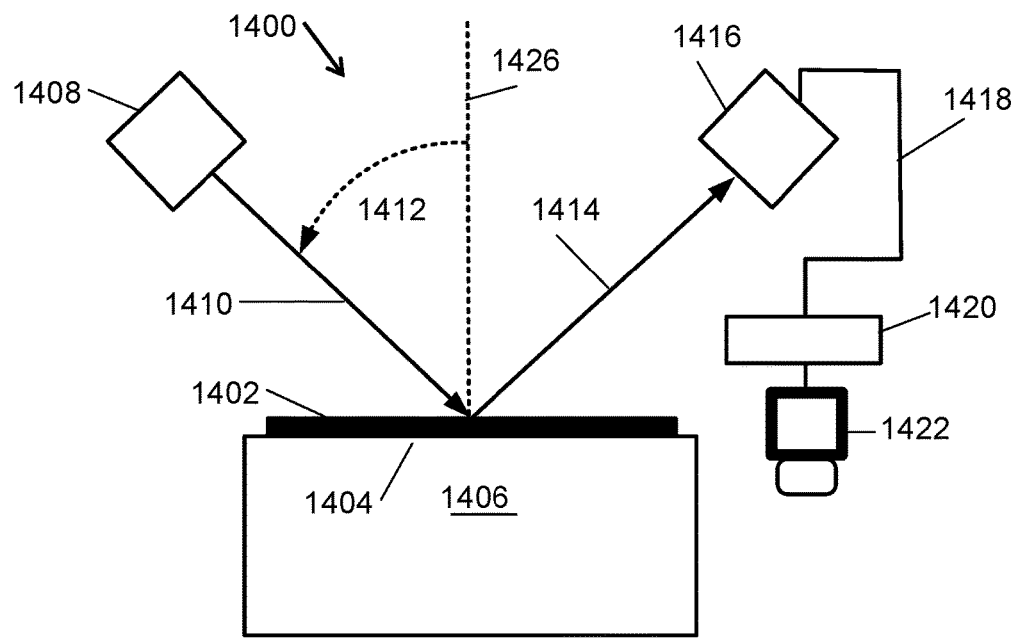
FIGS. 14A and 14B are diagrams of an exemplary reflection-type detection system.

FIG. 14A shows a side view of a reflection-type detection system 1400. In some implementations, the spatially ordered three-dimensional nanostructures are exposed to normal ambient (which may not carry the target materials) and may carry attached target materials that are obtained when the nanostructures were previously exposed to liquid or gaseous environments that may contain the target materials. The spatially ordered three-dimensional nanostructures are investigated by a polarized optical light beam as a function of the incidence angle and the azimuth angle of the incident beam. The light reflected from the substrate surface carrying the nanostructures is analyzed.

In some examples, spatially ordered three-dimensional nanostructures 1402 are formed on a front side 1404 of a substrate 1406. An optical system 1408 produces a collimated polarized light beam 1410 that approaches the front side 1404 at an oblique angle 1412 relative to a direction 1426 orthogonal to the front side 1404. The nanostructures 1402 are exposed to normal ambient (which may not carry the target materials) and may contain target materials that are obtained when the nanostructures were previously exposed to liquid or gaseous environments that contain the target materials. The reflected light beam 1414 is analyzed by a polarization sensitive instrument 1416 for its polarization state. The polarization state information is transmitted through an interconnect 1418 to a computer 1420 that processes the information. The computer 1420 may process the polarization state information and store the results in a data storage device. The propagation direction of the light beam 1410 is adjusted relative to the substrate 1406 so that measurements are performed for a range of incidence angles 1412.

Figure 14B:
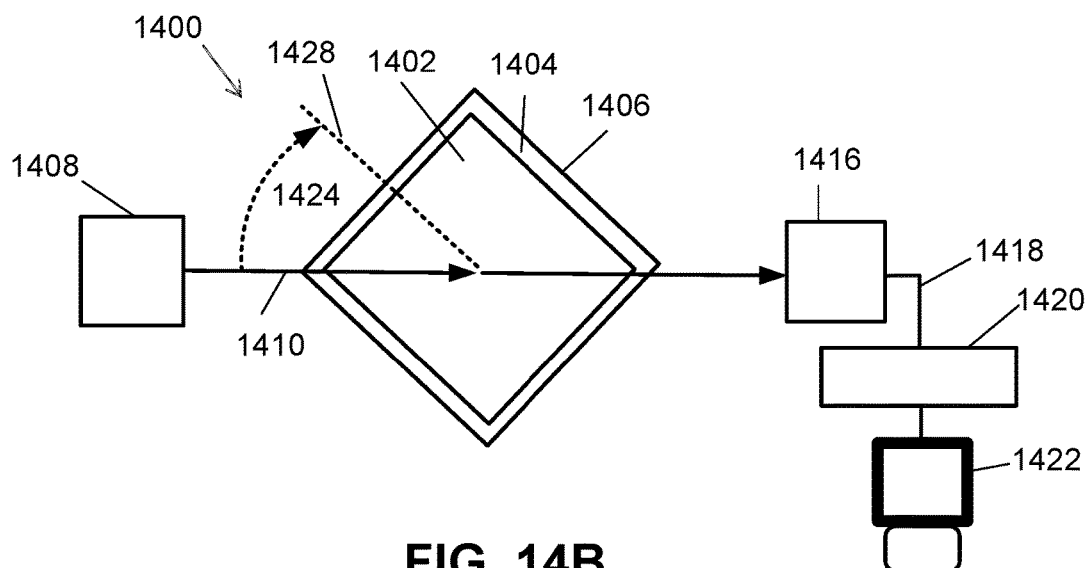

FIG. 14B shows a top view of the reflection-type detection system 1400. The collimated polarized light beam 1410 approaches the front side 1404 of the substrate 1406 at an azimuth angle 1424 relative to a reference direction 1428 parallel to the front side 1404. The substrate 1406 is rotated relative to the light beam 1410 so that measurements are performed for a range of azimuth angles 1424. After the measurements are performed for a predetermined range of incidence angles 1412 and azimuth angles 1424, the computer 1420 process all the measurements and may provide a graphical representation of the measurements, e.g., a $M^3$Scope image, that can be shown on a display 1420 or stored in the data storage device.

To determine whether target particles are attached to the nanostructures 1402, the measurements are compared to reference measurement data. In some implementations, the reference measurement data can be obtained by performing another set of measurements prior to exposing the nanostructures 1402 to the liquid or gaseous environment that contains the target materials. This set of measurements is stored for use as a reference for comparison with later measurements. Changes in the birefringence as determined from the later measurements relative to the birefringence as determined from the reference measurements may indicate a presence of target particles.

In some implementations, the substrate 1406 may have two regions having the same type of nanostructures in which a first region is exposed to the environment that may contain the target materials while a second region is not exposed to the environment. For example, the nanostructures in the second region may be covered by a material that blocks the target materials from interacting with the nanostructures in the second region, in which the material is transparent to the probe light so that the material does not affect the optical measurements. Measurements performed on the nanostructures in the second region can serve as reference values for comparison with the measurements on the nanostructures in the first region. Changes in the birefringence as determined from the measurements performed on the first region relative to the birefringence as determined from the measurements performed on the second region may indicate presence of target particles.

Figure 15:
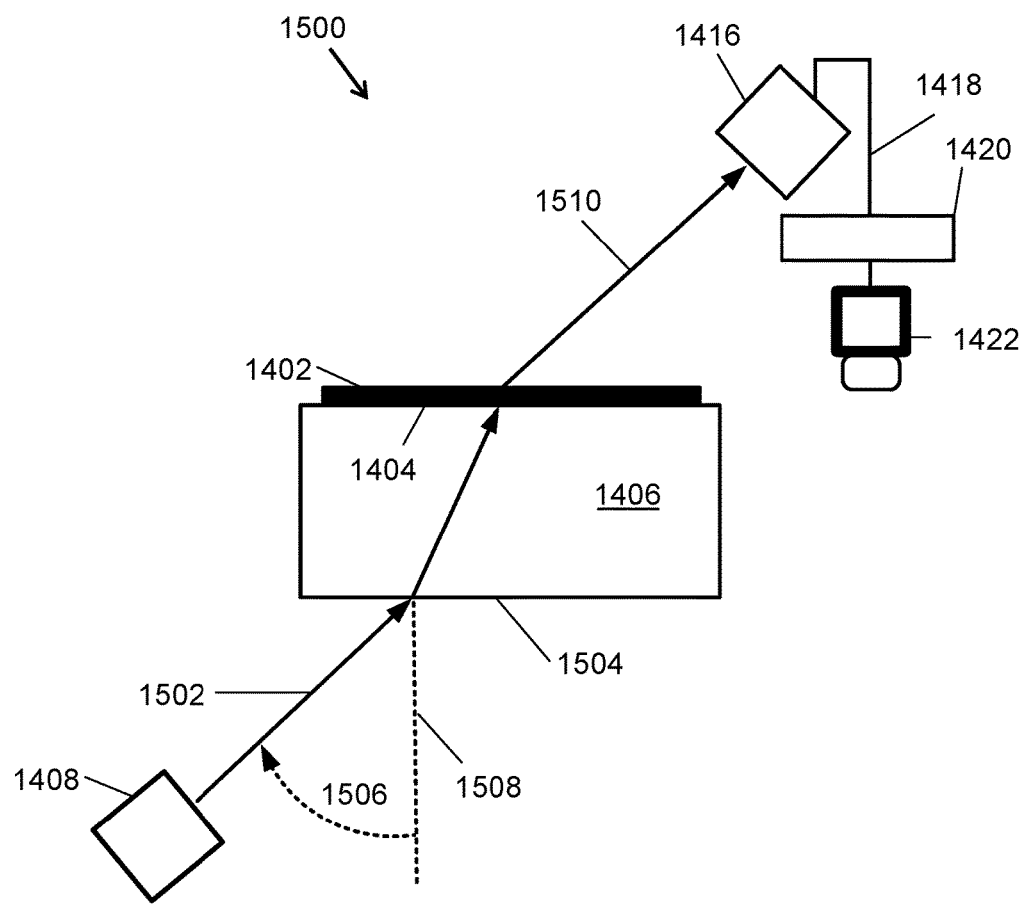
FIG. 15 is a diagram of an exemplary transmission-type detection system.

Referring to FIG. 15, a transmission-type detection system 1500 can be used to detect the presence of target particles. Similar to the example shown in FIG. 14A, in some implementations, the spatially ordered three-dimensional nanostructures are exposed to normal ambient and may carry attached target materials that are obtained when the nanostructures were previously exposed to liquid or gaseous environments that contain the target materials in diluted forms. The nanostructures are investigated by a polarized optical light beam as a function of the incidence angle and the azimuth angle of the incident beam. The light transmitted through the substrate and the substrate surface carrying the nanostructures is analyzed.

In some examples, an optical system 1408 produces a collimated polarized light beam 1502 that approaches a back side 1504 of a substrate 1406 at an oblique angle 1506 relative to a direction 1508 orthogonal to the back side 1504. The light beam 1502 passes through the substrate 1406 and transmits through a front side 1404 that have nanostructures 1402. The nanostructures 1402 are exposed to normal ambient and may contain target materials previously acquired. The transmitted light beam 1510 is analyzed by a polarization sensitive instrument 1416 for its polarization state. The polarization state information is transmitted through an interconnect 1418 to a computer 1420 that processes the information. The computer 1420 may process the polarization state information and store the results in the data storage device. The propagation direction of the light beam 1502 is adjusted relative to the substrate 1406 so that measurements are performed for a range of incidence angles 1506. Similar to the example show in FIG. 14B, the substrate 1406 is rotated relative to the light beam 1502 so that measurements are performed for a range of azimuth angles. After the measurements are performed for a predetermined range of incidence angles 1506 and azimuth angles, the computer 1420 process all the measurements and may provide a graphical representation of the measurements, e.g., a M³Scope image, that can be shown on the display 1420 or stored in a data storage device.

Figure 16:
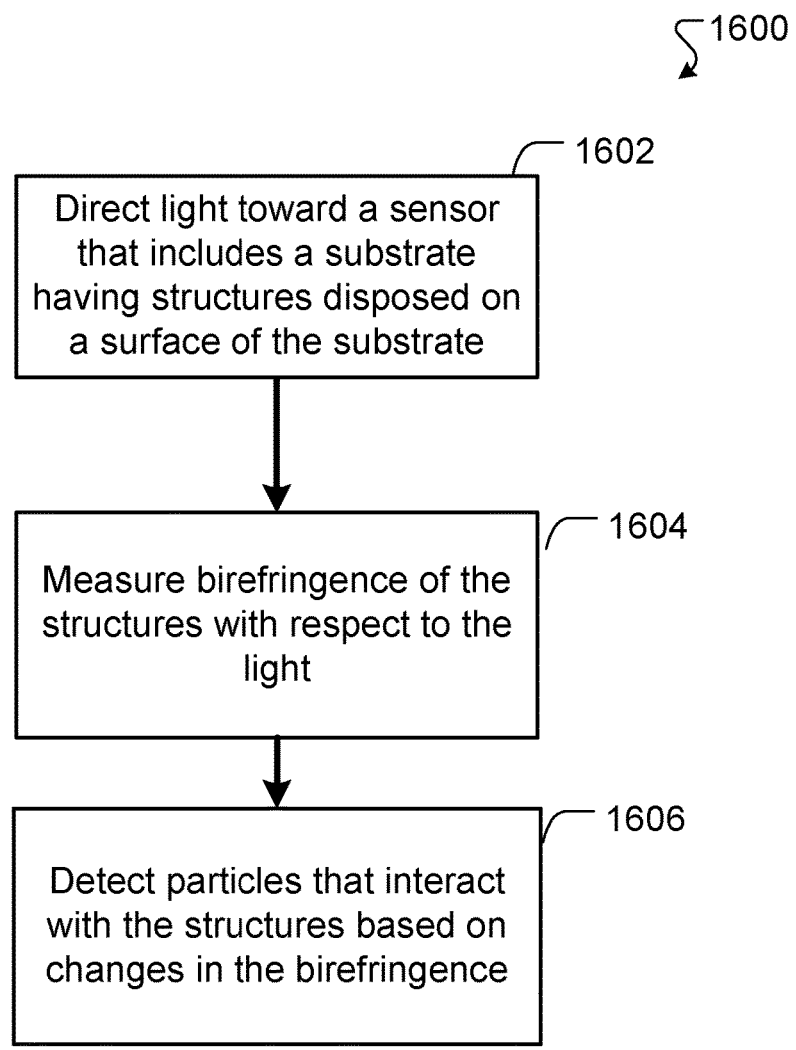
FIG. 16 is a flow diagram of a process for detecting target particles.

Referring to FIG. 16, a process 1600 for detecting target particles is provided. The process 1600 includes directing light toward a sensor that includes a substrate having structures disposed on a surface of the substrate (1602). For example, the light can be the light beam 1204 (FIG. 12), 1312 (FIG. 13), 1410 (FIG. 14A), or 1502 (FIG. 15). The substrate can be, e.g., the substrate 302 (FIG. 3A), 306 (FIG. 3B), 402 (FIG. 4), 502 (FIG. 5), 604 (FIG. 6), 612 (FIG. 7A), 1004 (FIG. 10), 1214 (FIG. 12), 1314 (FIG. 13), or 1406 (FIGS. 14A and 15). The structures can be, e.g., columns 102 (FIG. 1A), spirals 110 (FIG. 1B), staircase structures 120 (FIG. 1C), or chevron shaped structures.

The process 1600 can include measuring birefringence of the structures with respect to the light (1604). For example, the measurements can be performed in-situ, such as shown in FIGS. 12 and 13, or performed after the structures are removed from the environment containing the target particles, such as shown in FIGS. 14A, 14B, and 15. The measurements can be performed using light reflected from the surface of the substrate and does not pass through the substrate, such as shown in FIGS. 12 and 14A, or performed using transmitted light that passes through the substrate, such as shown in FIGS. 13 and 15.

The process 1600 can include detecting particles that interact with the structures based on changes in the birefringence (1606). For example, changes in the birefringence can be determined based analyzing M³Scope images. Other methods of analyzing birefringence may also be used.

Figure 17:
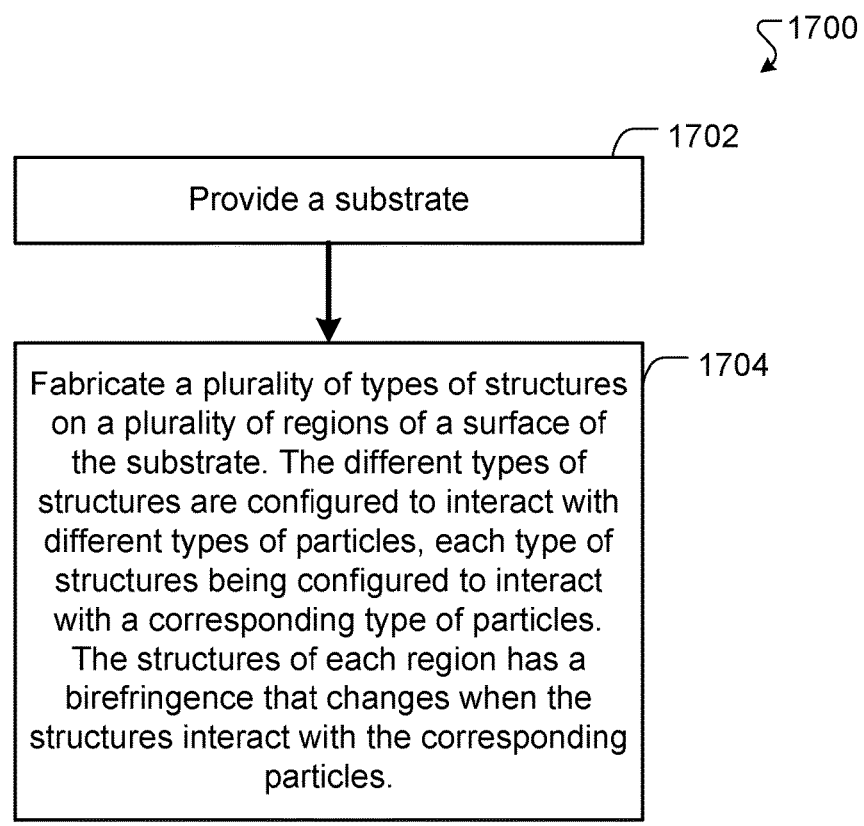
FIGS. 17 and 18 are flow diagrams of processes for fabricating sensors for detecting target particles.

Referring to FIG. 17, a process 1700 for fabricating a sensor for detecting target particles is provided. The process 1700 includes providing a substrate (1702). For example, the substrate can be the 604 (FIG. 6).

The process 1700 can include fabricating a plurality of types of structures on a plurality of regions of a surface of the substrate (1704). The different types of structures are configured to interact with different types of particles, each type of structures being configured to interact with a corresponding type of particles. The structures of each region have a birefringence that changes when the structures interact with the corresponding particles. For example, the plurality of regions can be the regions 602 (FIG. 6). The structures can be columns 102 (FIG. 1A), spirals 110 (FIG. 1B), staircase structures 120 (FIG. 1C), or chevron shaped structures.

Figure 18:
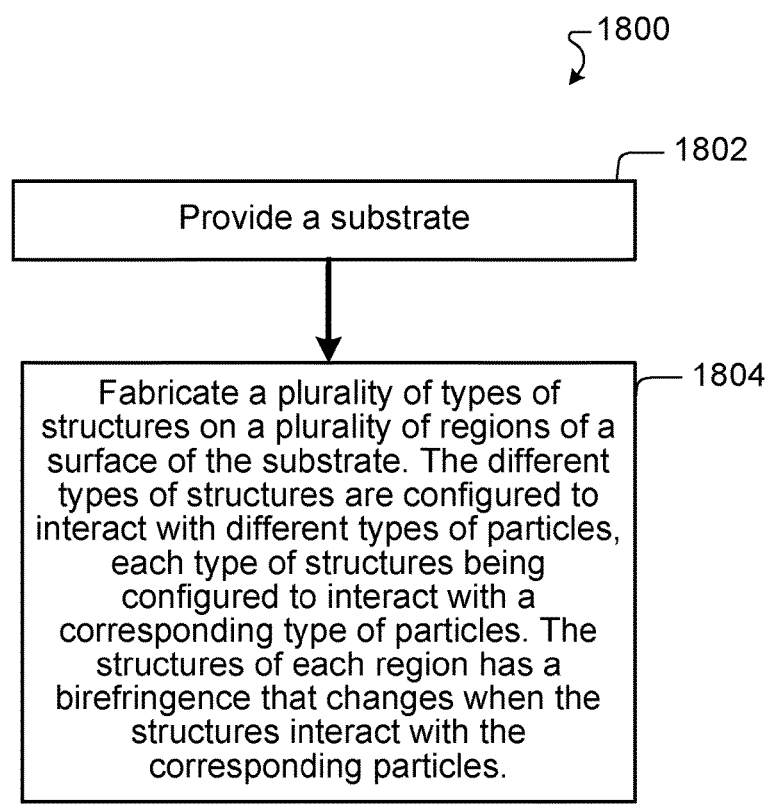

Referring to FIG. 18, a process 1800 for fabricating a sensor for detecting target particles is provided. The process 1800 includes fabricating structures on a surface of a substrate (1802). For example, the structures can be columns 102 (FIG. 1A), spirals 110 (FIG. 1B), staircase structures 120 (FIG. 1C), or chevron shaped structures. The substrate can be the substrate 302 (FIG. 3A), 306 (FIG. 3B), 402 (FIG. 4), 502 (FIG. 5), 604 (FIG. 6), 612 (FIG. 7A), 1004 (FIG. 10), 1214 (FIG. 12), 1314 (FIG. 13), or 1406 (FIGS. 14A and 15).

The process 1800 can include coating the structures with a layer of material to stabilize birefringence of the structures, in which the structures are configured such that the birefringence of the structures with respect to light changes when the structures interact with particles (1804). For example, the layer of material can be aluminum oxide. The layer of material can be formed by atomic layer deposition, as shown in FIG. 4.

The computers 1224 (FIG. 12), 1322 (FIG. 12), and 1420 (FIGS. 14A and 15) can be implemented by hardware or a combination of hardware and software. For example, the computers 1224, 1322, and 1420 may include one or more processors and one or more computer-readable mediums (e.g., RAM, ROM, SDRAM, hard disk, optical disk, and flash memory). The one or more processors can execute instructions to implement the functions performed by the modules of computers 1224, 1322, and 1420, such as generating and analyzing M³Scope images. The modules can also be implemented using application-specific integrated circuits (ASICs). The term "computer-readable medium" refers to a medium that participates in providing instructions to a processor for execution, including without limitation, non-volatile media (e.g., optical or magnetic disks), and volatile media (e.g., memory) and transmission media. Transmission media includes, without limitation, coaxial cables, copper wire and fiber optics.

The features described above can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language (e.g., C, Java), including compiled or interpreted languages, and it can be deployed in any form, including as a stand-alone program or as a module, component, subroutine, a browser-based web application, or other unit suitable for use in a computing environment.

Suitable processors for the execution of a program of instructions include, e.g., both general and special purpose microprocessors, digital signal processors, and the sole processor or one of multiple processors or cores, of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous. For example, multiple light beams may simultaneously probe different regions of a microarray, and information about the different regions may be processed in parallel.

Although some examples have been discussed above, other implementations and applications are also within the scope of the following claims. For example, the nanostructures can be functionalized by coating the nanostructures with noble metals. The nanostructures can be designed to interact with extracellular matrix so as to detect cell attachments. The nanostructures can be designed to detect exoskeletons of cells. In the example of FIG. 13, the front and back sides of the substrate do not have to be parallel to each other. Measurements of optical properties, such as birefringence, can be performed in addition to measurements of other properties of the nanostructures, such as mechanical resonances, magnetic resonances, piezoelectric resonances that vary upon interaction with target particles. The combination of the measurements of various properties of the nanostructures can enhance the accuracy of detection of the target particles. Detection of target particles can be performed based on detection of polarization states to quantify the anisotropy of the nanostructures.

What is claimed is:

1. An apparatus comprising:
a substrate; and
structures disposed on the substrate in which each of the structures has a functional layer configured to interact with a predetermined type of particles, and the structures have a birefringence that changes when the structures interact with the predetermined type of particles.

2. The apparatus of claim 1 in which the structures comprise nanostructures.

3. The apparatus of claim 1 in which the structures have dimensions ranging from 1 nanometer to 100 micrometers.

4. The apparatus of claim 1 in which the structures comprise at least one of columns, spirals, staircase structures, or chevron structures.

5. The apparatus of claim 1 in which the structures comprise slanted columns that extend along a direction at an angle relative to a surface of the substrate, the angle being less than 80 degrees.

6. The apparatus of claim 1 in which the structures are made of a material that reacts with air, and the structures are coated with thin films that are inactive to air.

7. The apparatus of claim 6 in which the material comprises cobalt and the thin films comprise aluminum oxide.

8. The apparatus of claim 6 in which the structures are coated with a material that comprises at least one of a metal, a metal oxide, a transition metal oxide, an alloy, a compound, or a polymeric network.

9. The apparatus of claim 6 in which the structures are coated with a material that comprise at least one of a dielectric material, a semiconducting material, an electrically insulating material, a ferroelectric material, or a magnetic material.

10. The apparatus of claim 1 in which the functional layers comprise at least one of chemical recognition elements or biochemical recognition elements that are configured to interact with the particles.

11. The apparatus of claim 1 in which the functional layers comprise recognition ligands.

12. The apparatus of claim 11 in which the recognition ligands include at least one of nucleic acid segments, aptamers, peptides, proteins, antibodies, cells, or carbohydrates.

13. The apparatus of claim 12 in which the proteins include fibronectin.

14. The apparatus of claim 1 in which the functional layers are configured to interact with an extracellular matrix of cells.

15. The apparatus of claim 1, comprising a light source to emit light that is directed toward the substrate, and a polarization sensitive detector to detect light reflected from the substrate or transmitted through the substrate.

16. The apparatus of claim 15, comprising a data processor to process signals from the detector to generate Mueller matrices, and analyze the Mueller matrices to detect changes in the birefringence of the structures.

17. The apparatus of claim 1 in which a first portion of the substrate has structures that interact with the particles, a second portion of the substrate has structures that do not interact with the particles, the structures in the second portion has a birefringence that is the same as the birefringence of the structures in the first portion prior to interacting with the particles, and the structures in the second portion has a birefringence that is different from the birefringence of the structures in the first portion upon interacting with the particles.

18. The apparatus of claim 1 in which the substrate has regions having different types of structures, each region has one type of structures, and each type of structures interact with a corresponding type of particles.

19. The apparatus of claim 18 in which the different portions differ in at least one of dimensions of the structures, shapes of the structures, spacing of the structures, or functional layers on the structures.

20. The apparatus of claim 1 in which the structures comprise at least one of a metal, a metal oxide, a transition metal oxide, an alloy, a compound, or a polymeric network.

21. The apparatus of claim 1 in which the structures comprise at least one of a dielectric material, a semiconducting material, an electrically insulating material, a ferroelectric material, or a magnetic material.

22. The apparatus of claim 1 in which the functional layer comprises at least one of aluminum oxide, titanium oxide, silicon oxide, hafnium oxide, ruthenium oxide, platinum, gold, silver, aluminum, ruthenium, or cobalt.

23. The apparatus of claim 1 in which the functional layer comprises at least one of self-assembled monolayers of organic molecules, self-assembled multiple layers of organic molecules, polymer-based surface coatings, oligonucleic acid, or peptide molecules.

24. The apparatus of claim 1 in which the functional layer comprises at least one of a polymer having one or more reactive functional groups, cationic polymer, lipid, or DNA complex.

* * * * *